US012241885B2

(12) United States Patent
Troxler

(10) Patent No.: US 12,241,885 B2
(45) Date of Patent: Mar. 4, 2025

(54) SYSTEMS AND METHODS FOR ASPHALT DENSITY AND SOIL MOISTURE MEASUREMENTS USING GROUND PENETRATING RADAR

(71) Applicant: Robert Ernest Troxler, Raleigh, NC (US)

(72) Inventor: Robert Ernest Troxler, Raleigh, NC (US)

(73) Assignee: International Research Institute

(*) Notice: Subject to any disclaimer, the term of this patent is extended or adjusted under 35 U.S.C. 154(b) by 181 days.

(21) Appl. No.: 17/730,671

(22) Filed: Apr. 27, 2022

(65) Prior Publication Data
US 2022/0252571 A1    Aug. 11, 2022

Related U.S. Application Data

(63) Continuation of application No. 16/206,188, filed on Nov. 30, 2018, now Pat. No. 11,346,835, which is a
(Continued)

(51) Int. Cl.
*G01N 33/42* (2006.01)
*E01C 19/23* (2006.01)
(Continued)

(52) U.S. Cl.
CPC ............ *G01N 33/42* (2013.01); *E01C 19/235* (2013.01); *G01N 9/24* (2013.01); *G01N 22/04* (2013.01);
(Continued)

(58) Field of Classification Search
CPC .......... G01N 33/42; G01N 9/24; G01N 22/04; G01N 33/246; E01C 19/235;
(Continued)

(56) References Cited

U.S. PATENT DOCUMENTS 3,784,905 A * 1/1974 Blackwell ............ G01N 27/223
324/687
4,814,690 A 3/1989 Melcher et al.
(Continued)

FOREIGN PATENT DOCUMENTS

EP        0971227 A1   1/2000
JP     2009002943 A   1/2009

OTHER PUBLICATIONS

A.K. Verman and Nasimuddin, Nondestructive Measurement of Complex Permittivity of Sheet Material, Microwave and Optical Technology Letters, Mar. 20, 2003, pp. 483-486, vol. 36, No. 6, Wiley Periodicals, Inc.
(Continued)

*Primary Examiner* — Marcus E Windrich
(74) *Attorney, Agent, or Firm* — Olive Law Group, PLLC

(57) ABSTRACT

Systems and methods for ground penetrating radar for determining thickness, density and moisture are therefore provided. According to an embodiment, a ground penetrating radar (GPR) system comprises a system controller configured to produce an electromagnetic signal for signal penetration of a pavement material. Further, the GPR system comprises a frequency modulated continuous wave controller. Further, the GPR system comprises an ultra wide band (UWB) antenna coupled to the system controller, wherein the UWB antenna is configured to transmit the produced electromagnetic signal to the pavement material and receive the electromagnetic signal as a reflection from the pavement material. Further, the system controller is further configured to receive the electromagnetic signal from the UWB antenna.

23 Claims, 11 Drawing Sheets

Related U.S. Application Data continuation of application No. 14/214,629, filed on Mar. 14, 2014, now Pat. No. 10,145,837.

(60) Provisional application No. 61/786,060, filed on Mar. 14, 2013.

(51) Int. Cl.
| | | |
|---|---|---|
| *G01N 9/24* | (2006.01) | |
| *G01N 22/04* | (2006.01) | |
| *G01N 33/24* | (2006.01) | |
| *G01S 13/02* | (2006.01) | |
| *G01S 13/32* | (2006.01) | |
| *G01S 13/88* | (2006.01) | |
| *G01V 3/12* | (2006.01) | |

(52) U.S. Cl.
CPC ........ *G01N 33/246* (2013.01); *G01S 13/0209* (2013.01); *G01S 13/32* (2013.01); *G01S 13/885* (2013.01); *G01V 3/12* (2013.01)

(58) Field of Classification Search
CPC .... G01S 13/0209; G01S 13/32; G01S 13/885; G01V 3/12
See application file for complete search history.

(56) References Cited

U.S. PATENT DOCUMENTS

| | | | |
|---|---|---|---|
| 4,979,197 A | 12/1990 | Troxler et al. | |
| 4,991,915 A | 2/1991 | Thompson et al. | |
| 5,334,941 A | 8/1994 | King | |
| 5,384,715 A | 1/1995 | Lytton | |
| 5,554,935 A | 9/1996 | Kraszewski et al. | |
| 5,614,670 A * | 3/1997 | Nazarian | G01M 7/08 73/146 |
| 5,666,061 A | 9/1997 | Assenheim | |
| 5,673,050 A * | 9/1997 | Moussally | G01S 13/0209 342/25 F |
| 5,835,053 A | 11/1998 | Davis | |
| 5,900,736 A * | 5/1999 | Sovik | G01N 9/24 324/687 |
| 5,939,889 A * | 8/1999 | Zoughi | G01N 33/28 324/643 |
| 5,952,561 A * | 9/1999 | Jaselskis | G01N 33/42 73/78 |
| 6,008,757 A * | 12/1999 | Boulianne | G01S 19/51 342/357.29 |
| 6,147,503 A | 11/2000 | Nelson et al. | |
| 6,177,903 B1 | 1/2001 | Fullerton et al. | |
| 6,215,317 B1 | 4/2001 | Siddiqui et al. | |
| 6,414,497 B1 * | 7/2002 | Sovik | G01N 27/02 324/687 |
| 6,460,006 B1 * | 10/2002 | Corcoran | E01C 19/288 404/117 |
| 6,577,141 B2 | 6/2003 | Gandrud | |
| 6,617,861 B1 | 9/2003 | Joshi | |
| 6,803,771 B2 * | 10/2004 | Sovik | G01N 9/00 324/654 |
| 6,973,821 B2 * | 12/2005 | Corcoran | G01N 9/36 73/78 |
| 6,987,393 B2 * | 1/2006 | Jean | G01N 22/00 324/710 |
| 7,219,024 B2 * | 5/2007 | Gamache | G01N 27/028 702/182 |
| 7,226,239 B2 * | 6/2007 | Stridiron | E01C 19/288 404/84.1 |
| 7,239,150 B2 | 7/2007 | Troxler et al. | |
| 7,591,608 B2 * | 9/2009 | Hall | E01C 19/22 404/133.05 |
| 7,731,450 B2 * | 6/2010 | Congdon | E01C 19/288 701/50 |
| 2002/0075006 A1 | 6/2002 | Goldfine et al. | |
| 2002/0175691 A1 * | 11/2002 | Sovik | G01N 33/42 324/654 |
| 2002/0190728 A1 * | 12/2002 | Gandrud | G01N 33/42 324/663 |
| 2004/0032269 A1 * | 2/2004 | Sovik | G01N 33/42 324/663 |
| 2004/0073382 A1 | 4/2004 | Troxler et al. | |
| 2006/0106546 A1 * | 5/2006 | Roberts | G01N 22/04 702/27 |
| 2006/0226857 A1 * | 10/2006 | Troxler | G01R 35/007 324/663 |
| 2007/0188177 A1 * | 8/2007 | Troxler | G01N 33/38 324/643 |
| 2007/0201951 A1 * | 8/2007 | Stridiron | G01N 9/24 404/84.1 |
| 2007/0235250 A1 * | 10/2007 | Krumhansl | G01V 1/047 181/121 |
| 2011/0260736 A1 * | 10/2011 | Troxler | G01R 35/007 324/601 |

OTHER PUBLICATIONS

Al-Qadi et al. "Effect of Moisture on Asphaltic Concrete at Microwave Frequencies," IEEE Transactions on Geoscience and Remote Sensing, IEEE, Inc., vol. 29, No. 5 Sep. 1, 1999, pp. 710-717.

C. Richard Liu et al., "Pavement Thickness Measurement Using FM-CW Radar", Optical Sensing II, vol. 4491, Nov. 27, 2001, XP055302206, 1000 20th St. Bellignham WA 98225, ISSN: 0277-786X, DOI: 10.1117/12.450157, ISBN: 978-1-62841-971-9.

Chudodiak WR et al., "Recent advances in broad-band VHF and UHF transmission line methods for moisture content and dielectric constant measurement," IEEE Transactions on Instrumentation and Measurement USA, vol. IM-28, No. Dec. 4, 1979, pp. 284-289.

Curtis, Jo, "A durable laboratory apparatus for the measurement of soil dielectric properties," IEEE Transactions on Instrumentation and Measurement IEEE USA, vol. 50 No. 5, Oct. 2001, pp. 1364-1369.

Edward J. Jaselskis, Roller-Mountable Asphalt Pavement Qaulity Indicator Using Differential Microwave Signals, NCHRP-IDEA Project 44, pp. 62-64, 1998.

Effect of Water and Temperature on Hot Mix Asphalt Density Measurement Using Electromagnetic Sensing, Trans Tech Systems, Inc., Technical Note 0301, pp. 1-4, Jan. 15, 2003.

EPO Search Report, Application No. 14768430.2, related PCT Application No. PCT/US2014/029830 dated Sep. 26, 2016.

Final Office Action issued in counterpart U.S. Appl. No. 14/214,629 dated May 9, 2017.

Hipp JE, "Soil electromagnetic parameters as functions of frequency, soil density and soil moisture," Proceeds of the IEEE USA, vol. 62, No. 1, Jan. 1974, pp. 98-103.

Huaquig Liang, et al., "Study on Signal Processing of FMCW Ground Penetrating Radar", Measuring Technology and Mechatronics Automation, ICMTMA 09., International Conference on, IEEE, Piscataway, NJ, US, Apr. 11, 2009 pp. 528-531, XP031511276, ISBN: 978-0-7695-3583-8.

Janezic MD et al., "Complex permittvity determination from propagation constant measurements" IEEE Microwave and Guided Wave Letters, IEEE USA, vol. 9, No. 2, Feb. 1999, pp. 76-78.

Kamal Sarabandi, Microstrip Ring Resonator for Soil Moisture Measurements, IEEE Transactions of Geoscience and Remote Sensing, Sep. 1997, pp. 1223-1231, vol. 35 No. 5.

Li E. S. et al., Low grazing incidence millimeter-wave scattering models and measurements for various road surfaces, IEEE Transactions on Antennas and Propagation IEEE USA, vol. 47, No. 5, May 1999, pp. 851-861.

Non-Final Office Action issued in counterpart U.S. Appl. No. 14/214,629 dated Aug. 19, 2016.

Non-Final Office Action issued in counterpart U.S. Appl. No. 14/214,629 dated Dec. 12, 2017.

Notice of Allowability issued in counterpart U.S. Appl. No. 14/214,629 dated Aug. 31, 2018.

Notice of Allowance issued in counterpart U.S. Appl. No. 14/214,629 dated Aug. 31, 2018.

(56) References Cited

OTHER PUBLICATIONS

PCT Search Report and Written Opinion for PCT International Application No. PCT/US2014/029830, dated Jul. 28, 2014.
Request for Continued Examination filed in counterpart U.S. Appl. No. 14/214,629 dated Nov. 9, 2017.
Response to Non-Final Office Action filed in counterpart U.S. Appl. No. 14/214,629 dated Feb. 21, 2017.
Response to Non-Final Office Action filed in counterpart U.S. Appl. No. 14/214,629 dated May 14, 2018.
Richard D. Hollinger, K.A. Jose, Anilkumar Tellakula, V.V. Varadan and V.K. Varadan, Microwave Characterization of Dielectric Materials from 8 to 1000 GHz Using a Free-Space Setup, Microwave and Optical Technology Letters, Jul. 20, 2000, pp. 100-105, vol. 26, No. 2 John Wiley & Sons, Inc.
S.S. Stuchly and C.E. Bassey, Microwave Coplanar Sensors for Dielectric Measurements, Meas. Sci. Technol. 9, 1998, pp. 1321-1329, IOP Publishing Ltd., 1998.
Saarenketo Timo et al., "Road evaluation with ground penetrating radar," J Appl Geophys; Journal of Applied Geophysics, Mar. 2000, vol. 43, No. 2-4, May 27, 1998, pp. 199-138.
Samir Trabelsi, Andrezej W. Krazsewki, Stuart O. Nelson, New Density-Independent Calibration Function for Microwave Sensing of Moisture Content in Particulate Materials, IEEE Transactions of Geoscience and Remote Sensing, Jun. 1998, pp. 613-622, vol. 47, No. 3.
TransTech Systems Pavement Quality Indicator (PQI) Technical Application Brief, Trans Tech, pp. 1-4, Jan. 2003.
TransTechn Systems' Soil Quality Indicator (SQI) Application Brief, Jan. 2003.
U.S. Non-Final Office Action for U.S. Appl. No. 10/971,546 dated Dec. 30, 2005.
U.S. Non-Final Office Action for U.S. Appl. No. 10/971,546 dated Jun. 5, 2006.
Communication pursuant to Article 94(3) EPC issued in counterpart EP Application No. 14 768 430.2 dated Mar. 26, 2019 (4 pages).
Communication pursuant to Article 94(3) EPC from the EPO re counterpart application 14768430.2 issued Oct. 14, 2020 (4 pages).

\* cited by examiner

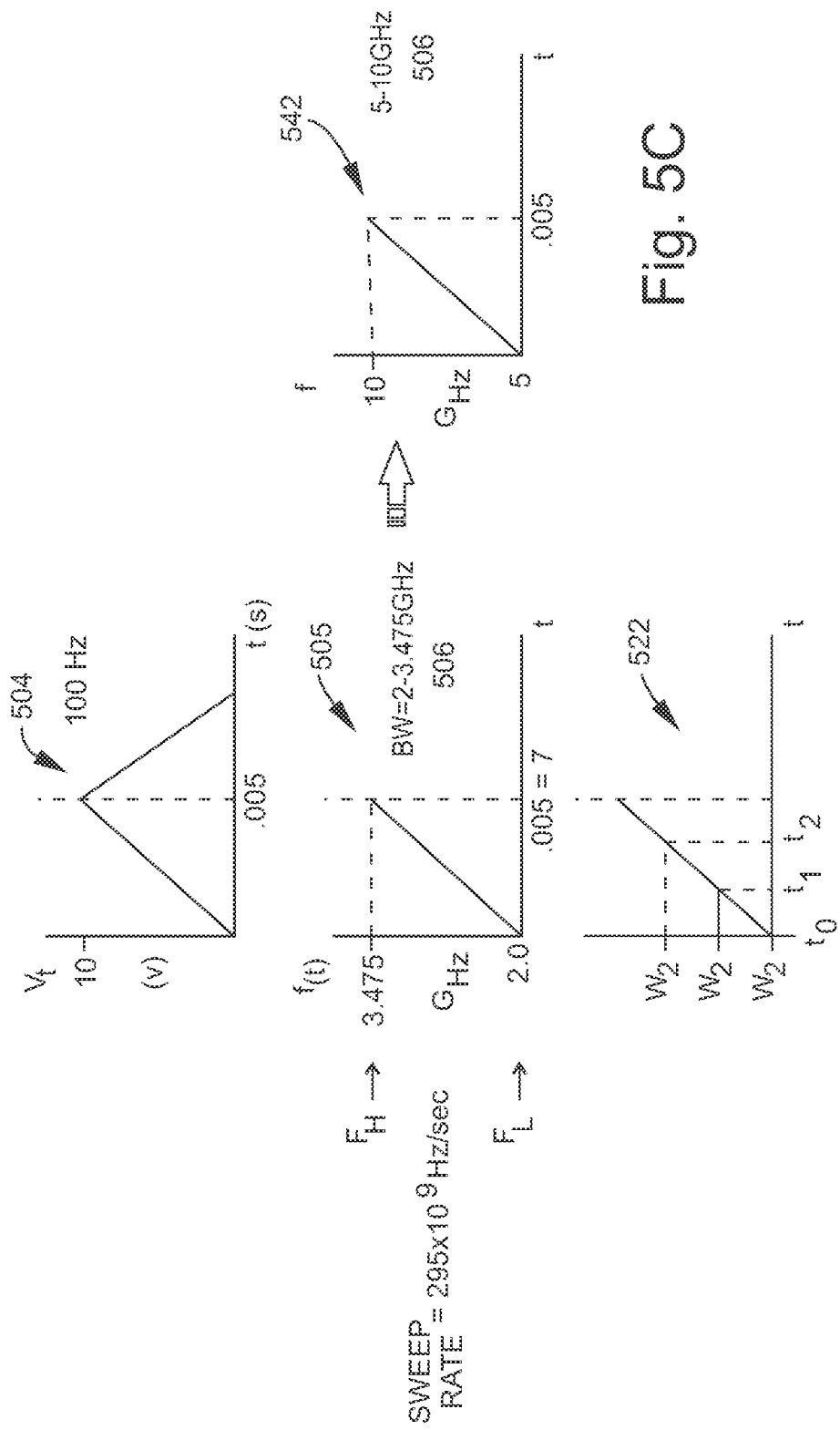

SYSTEMS AND METHODS FOR ASPHALT DENSITY AND SOIL MOISTURE MEASUREMENTS USING GROUND PENETRATING RADAR

CROSS REFERENCE TO RELATED APPLICATIONS

This is a continuation application of U.S. patent application Ser. No. 16/206,188, filed Nov. 30, 2018, and titled SYSTEMS AND METHODS FOR ASPHALT DENSITY AND SOIL MOISTURE MEASUREMENTS USING GROUND PENETRATING RADAR, which claims the benefit of U.S. patent application Ser. No. 14/214,629, filed Mar. 14, 2014, titled SYSTEMS AND METHODS FOR ASPHALT DENSITY AND SOIL MOISTURE MEASUREMENTS USING GROUND PENETRATING RADAR, and issued on Dec. 4, 2018 as U.S. Pat. No. 10,145,837, which claims the benefit of U.S. Provisional Patent Application No. 61/786,060, filed Mar. 14, 2013 and titled PAVEMENT MATERIAL MICROWAVE DENSITY MEASUREMENT METHODS AND APPARATUSES, the contents of which are hereby incorporated herein by reference in their entireties.

TECHNICAL FIELD

The present invention relates to asphalt density and soil moisture measurements using ground penetrating radar, and more particularly to a test instrument and method for measuring or correlating the density of an asphalt pavement sample using the reflection of high frequency signals from pavement material. The present invention also relates to measuring the free water content of construction materials.

BACKGROUND

Pavement materials, such as soil, sand, aggregate, asphalt, and cement, require quality testing for qualities such as moisture and density. Destructive tests and nondestructive tests are used throughout the industry for determining these qualities. In laboratory destructive tests, cylindrical samples are prepared, typically with a gyratory compactor, and various material properties are studied to determine the best mix design for a pavement. In field destructive tests, cylindrical samples are cored from test strips, newly constructed roads, or existing roads. The material properties of these samples are then used to evaluate whether the test strip or the new pavement meets the design criteria and whether the existing road is in good operating condition or in need of repairs. Currently, several methods are used for measuring the density of cylindrical samples: dimensional analysis, the water displacement method, the paraffin coated method, the vacuum sealed method, and the para-film-covered method. In each case, the bulk density of a sample is derived by, as in the definition, dividing the dry sample mass by the estimated sample volume. All methods require a balance with a sensitivity of 0.1 gram (g) to measure the mass of the sample. In the dimensional analysis method, sample volume is determined from the radius and thickness (height) measurements. In this example, many readings of the radius and thickness of the sample are made using either manually a Vernier caliper or automatically using a laser system. The average values of the radius and the thickness are then used to calculate the sample volume. This method overestimates the volume thus underestimating the density as it does not fully account for the surface features of the aggregate mix boundary.

Other methods use the Archimedes Principle for determining the sample volume. These methods require a large container filled with clean water. The water temperature may be monitored and controlled at a specific temperature, e.g. at 25° C. At one stage of the test, the sample is kept immersed in water for approximately 4 minutes and the weight of the sample, while suspended in water, is recorded. In the "paraffin-coated" method, after determining the dry weight of the sample, a thin coating of paraffin is applied to cover the entire surface area of the sample. Then, the sample is weighed again in air. Finally, the sample is weighed while immersed in water. More details can be found in standards ASTM D 2726 for the water displacement method and ASTM D 1188 for the paraffin-coated method.

Nondestructive field measurements of asphalt are typically accomplished with nuclear gauges. Nuclear radiation gauges have been widely used for measuring the density of soil and asphaltic materials. Such gauges typically include a source of gamma radiation which directs gamma radiation into the test material, and a radiation detector located adjacent to the surface of the test material for detecting radiation scattered back to the surface. From this detector reading, a determination of the density of the material can be made. Nuclear gauges, however, require a high degree of training and radiological management for the operators of these gauges. Therefore, it would be desirable to obtain accurate field measurement gauges without the use of nuclear gauges.

SUMMARY

The present invention relating to asphalt density and soil moisture measurements using ground penetrating radar are therefore provided. According to an embodiment a ground penetrating radar system comprises a system controller configured to produce an electromagnetic signal for signal penetration and scattering of a pavement material. Further, the GPR system comprises a frequency modulated continuous wave controller. Further, the GPR system comprises an ultra wide band (UWB) antenna coupled to the system controller, wherein the UWB antenna is configured to transmit the produced electromagnetic signal to the pavement material and receive the electromagnetic signal as a reflection from the pavement material. Further, the system controller is configured to receive the electromagnetic signal from the UWB antenna.

According to one embodiment of the invention, a method of obtaining a material property of a pavement material from a microwave field generally includes generating and propagating a microwave frequency electromagnetic field about the pavement material. The returned waveform or reflection of the electromagnetic wave from the pavement material can be measured, and the constitutive parameters of the pavement can be determined such as by network analysis or electronic methods. One example of measuring these constitutive parameters may include obtaining scattering parameters from the frequency response of the system, although other electronic response parameters may be employed. The measurement of the constitutive parameters permits correlating the constitutive parameters such as the dielectric properties to a material property of the pavement material sample, such as the density. Generally, the permittivity of a material permits direct correlation to the density of a material, and permittivity is a convenient way to assess density.

However, the response may be used to directly or indirectly calculate the density and moisture by other methods associated with the constitutive parameters of the construction material including complex permittivity, permeability, and conductivity.

According to an additional embodiment of the invention, a method may also include calibration techniques. Calibration may be accomplished by generating a microwave frequency electromagnetic field of a first mode about a calibration material. The calibration material may have known physical properties such as density, volume, thickness and moisture content. Similar to the measurement method, a frequency response of the calibration material may be determined. The frequency response of the calibration material may be correlated to the known physical properties of the calibration material, thus providing calibration curves for the frequency response of the pavement material. The calibration materials may be actual pavement samples, or materials with similar frequency responses such as stimulants including liquids, solids, gases and composites.

A method of correcting for the roughness of a pavement material is also provided. Generally the roughness may permit dividing the pavement into the near surface layer, the rough part, and below the surface layer. Accordingly, a method of determining the permittivity of a pavement material having a surface layer and a thickness generally includes measuring a pavement material with first and second frequencies. The first frequency reflection measures the permittivity in a sample volume corresponding to at least a portion of both the surface and more substantially below, the second frequency reflection responds to the permittivity in a sample volume corresponding at least a portion of the shallow or surface layer. This shallow layer has a different scattering mechanism to the higher frequencies as a result of the surface roughness. A calibration data set may be obtained for the first and second frequency responses by calibrating to a plurality of known pavement material permittivities and conditions. The first frequency response measures the permittivity over the pavement material to permit determining a first measured permittivity response. The second frequency response over the pavement material to permit determining a second measured permittivity response. The first permittivity and second permittivity are correlated with the calibration data to determine the permittivity property of the pavement material.

Additionally, embodiments of the invention include an apparatus for obtaining the density of a pavement sample. The apparatus generally includes a microwave antenna of a size and shape to generate an electromagnetic field about a pavement material of the proper field orientation. Sweeping frequency generators and electronic receiving circuitry are interconnected to the microwave system to generate a microwave input to the circuit for generating the electromagnetic field, and for conditioning and analyzing the response relative to the generated field. The analyzer may be capable of measuring at least one scattering parameter or reflection waveform or response. From the measured scattering parameter, the apparatus may determine the density or moisture of the pavement material, depending on the calibration selected. The system can be air or ground coupled, and used for spot checking or real time data analysis as when mounted to a compacting machine or vehicle. Interfacing the data with a database associated with an intelligent compaction device allows for integration of density, thickness and moisture for quality control of pavement materials.

An object of the presently disclosed subject matter having been stated herein above, and which is achieved in whole or in part by the presently disclosed subject matter, other objects will become evident as the description proceeds when taken in connection with the accompanying drawings as best described herein below.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings:

FIG. 5B is a block diagram and graph showing the voltage controlled signal from the voltage controlled oscillator;

FIG. 5C is a graph showing frequency of the voltage controlled signal as a function of time;

DETAILED DESCRIPTION

Figure 1:
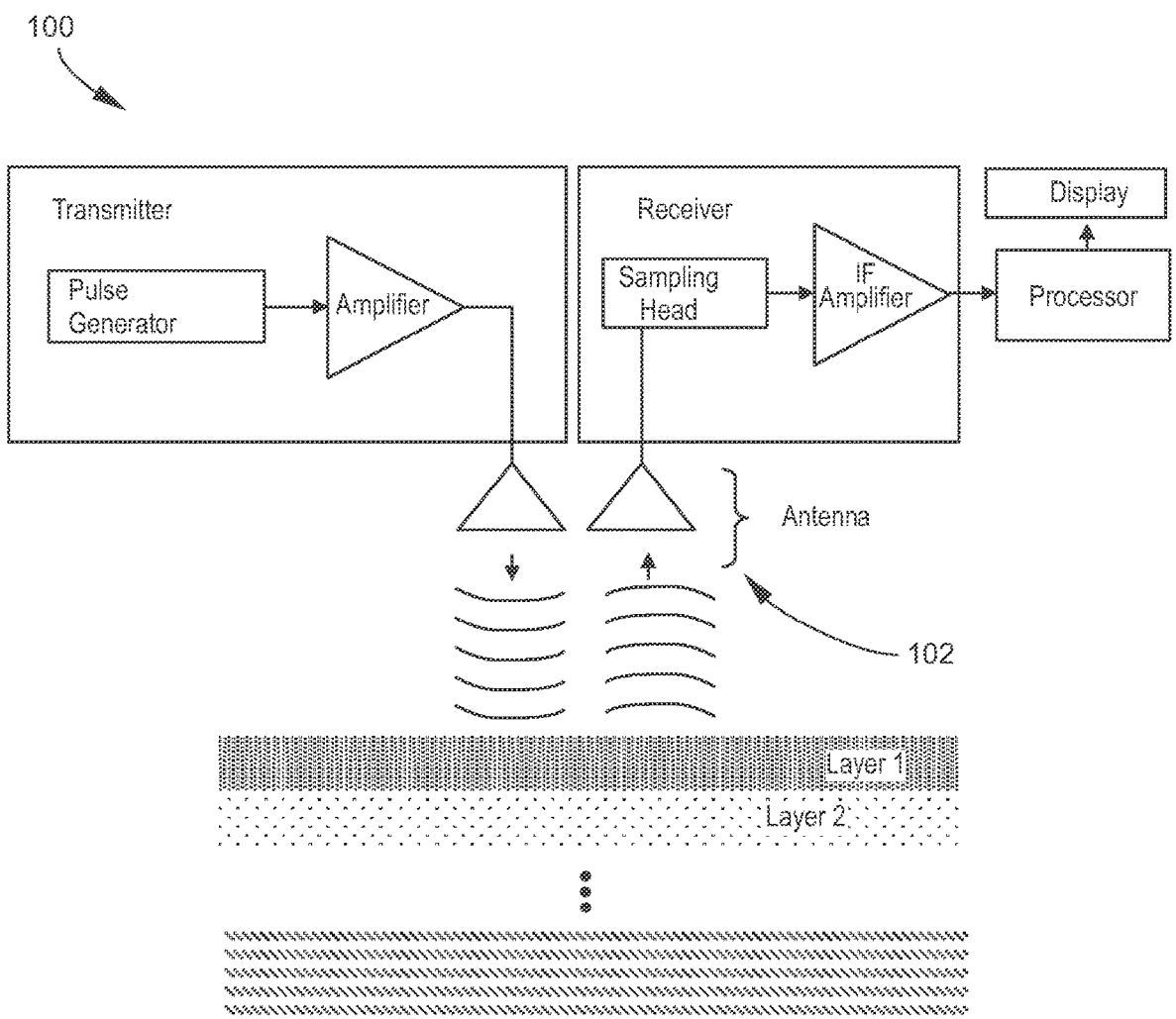
FIG. 1 is a block diagram showing a ground penetrating radar system configured as a bistatic system using two antenna systems.

The present inventions now will be described more fully hereinafter with reference to the accompanying drawings, in which some, but not all embodiments of the inventions are shown. Indeed, these inventions may be embodied in many different forms and may not be construed as limited to the embodiments set forth herein; rather, these embodiments are provided so that this disclosure will satisfy applicable legal requirements. Like numbers refer to like elements throughout.

Pavement materials, asphalt in particular, are heterogeneous mixtures of air, rocks, and binder. Each of these materials has a particular permittivity (i.e. the dielectric constant) associated with its ability to be polarized by an electric field. The permittivity is linearly related to the polarizability and is a complex quantity. The permittivity is generally complex having real, $\varepsilon'$, and imaginary components, $\varepsilon''$, representing energy storage and energy loss respectively to a propagating electromagnetic wave. Typically, when speaking of the dielectric constant one is referring to the real part of the permittivity which can be frequency dependent depending of the frequencies of interest.

Asphalt pavement is a mixture of air, rocks, and binder. Each of these materials has a particular permittivity (i.e. the dielectric constant) associated with its ability to be polarized by an electric field. The permittivity is linearly related to the polarizability. Air has a real relative permittivity of 1.0, asphalt binders have a real permittivity between 2.0 and 4.0, and rocks have permittivities that vary, but granite is about 4.0. Free water has a dielectric constant of 80 or less depending on the temperature. For HMA (hot mix asphalt), if moisture is present, the water is bound to the aggregate and has a dielectric constant near 3 or 4. This is close to the permittivity of the binder and dry aggregates, and is not problematic as long as it is consistent in the mix. In a moisture measuring mode, the microwave radar device would be used to measure the volume or mass percent of free water. The permittivity is generally complex having real, $\varepsilon'$, and imaginary components, $\varepsilon''$, representing energy storage and energy loss respectively to a propagating electromagnetic wave.

The permittivity of a material depends on the type of charge carrier that is being displaced by an applied electric field. These charge carriers are displaced thus forming a net dipole moment. The charges can be electronic, atomic, polar and ionic. In asphalt, all of the above mechanisms contribute to the apparent dielectric constant. However, the main contributions are due to the polar and ionic responses, on a per unit volume basis. Additional solvents or impurities such as water will increase these contributions and the apparent dielectric constant. For low frequencies, the heavy ions respond and the Maxwell-Wagner effect makes the asphalt appear strongly polar and temperature dependent. At microwave frequencies, this effect is nonexistent for HMA materials.

The behavior of polar molecules in the asphalt follows a frequency-temperature response that can be modeled with a modified Debye equation. The dispersion in the microwave region is significantly decreased as a result of the reduction of a relaxation frequency. This reduction is anticipated due to the heavy asphalt molecules, and because of the asphalt bonding to the aggregate, which is the purpose of adding the binder.

One well known method of measuring real and imaginary parts of permittivity is known to those of ordinary skill in the art and defined by ASTM Standard D2520-95, which is hereby incorporated by reference. The test method of D2520 is based on microwave measurement of the complex scattering parameters throughout a specimen in a resonant transmission line or closed cavity. The systems and methods herein incorporate these teachings and can further be extended to leaky type resonators. The measurements may be implemented by analyzing the wave propagation through the material specimen using S-parameter analysis. S-parameter analysis techniques may be accomplished by a variety of commercially available broadband network analyzers, such as the HP (Agilent) 8753 Network Analyzer manufactured by Agilent Technologies, Inc. of Palo Alto, California Network analyzers are well known to those of ordinary skill in the art for measuring the voltage standing wave ratio, complex reflection/transmission coefficients, high frequency impedance and return and insertion loss of a device under test. The setup typically includes a transmission/reflection test set consisting of sampling couplers or bridges, and the device under test, which is described in detail below. Here, the outgoing wave is sampled with the forward sampling coupling circuit while being isolated from the return reflection. The return is sampled in the same manner. The ratio of these defines the S parameter such as the reflection or transmission properties. These instruments are capable of both frequency and time domain analysis. For example, an impulse response can be analyzed for dispersion and velocity. The velocity is inversely related to the real part of the dielectric constant and proportional to $1/\sqrt{\varepsilon'}$ whereas the dispersion is related to the imaginary part $\varepsilon''$. It is now possible to economically build and design two port and full two port network analyzers that are compact and efficient on battery power. There are many designs that may be used for the network analysis including scalar and vector network analyzers, some use simple diode detectors as can be found in publications like "Microwave Impedance Measurement by P. I. Somlo, B S J. D. Hunter, Peter Peregrinus Lt., London UK. 1985, or Microwave Measurement Edited by A. e. Bailey, Peter Peregrinus Lt., London UK. 1985.

Impedance, permittivity, permeability, complex permittivity, and complex permeability of a material can be measured using S-parameter analysis, such as described in Agilent AN 154 S-parameter Design Application Note, which is hereby incorporated by reference. As S-parameters relate ratios of RF network inputs to outputs, they can be used to measure the ratios of RF network inputs and outputs for a material placed within a closed chamber or near an open sensor system. An incident RF electromagnetic wave is actively excited and the system responds according to the boundary conditions and constitutive relations of the material. For example, S11 is a reflection measurement from the device under test. S12 is a transmission measurement through the device under test. As such, S11 and S12 may be measured as a ratio of the RF input and output, in magnitude and phase. Hence the invention employs a density and/or moisture measuring system comprising a microwave radar sensor, means for coupling the energy to the sensor, propagating the energy to the surface of the pavement material, reflecting the energy from the material based on scattering and the permittivity boundary of the air and pavement and investigating the return signal in the time or frequency domain. The system incorporates a means for placing the sensor in the proximity of the construction pavement surface, and a measuring circuit allowing $S_{11}$, or return parameters to be obtained and displays using a data processing unit with software. The system uses a microwave sweeping oscillator and means to measure the parameters such as the Scattering matrix as a function of frequency or time, such as to locate maximum or minimum of S11 or S21 as a function of frequency and time. The display and software may be integrated into a single unit much like a Troxler 3440 Nuclear gauge, or the processing unit and display may be linked to a smart phone or hand held commuting device using a wire or wireless connection such as BLUETOOTH®. The software would include all the basic commands in addition to project management programs. The means for placing the sensor in the proximity of the asphalt surface MAY therefore be attached or added to a compaction device such as a rolling compactor for asphalt and soil and concrete. The compactors may be intelligent compactors (IC) and the radar compaction monitor/soil moisture monitor data output can be streamed in real time to the IC information data base. By selecting a calibration routine, a single ground penetrating radar system MAY be incorporated into measuring the density or quality indication of newly applied asphalt or roller compacted concrete. The same multiple use radar can also be incorporated into measuring the moisture content of a particular soil, sub base or embankment by proper selection of the moisture calibration curve for that material. Calibration methods include placing samples into devices to obtain relationships between the electromagnetic constitutive parameters and the mechanistic or volumetric properties. In field offsets, calibrations can be defined by offsetting a typical calibration curve via measurements of the quality indicator in situ by means of core samples, nuclear density measurements, and moisture measurements using other methods. In one example, actual pavement samples are placed into a resonant cavity and the permittivity is measured as a function of the pavement quality indicator such as density, modulus or moisture. Then calibration curves using a regression technique are incorporated to define permittivity vs. density, modulus, (or moisture). Next the radar system is calibrated using samples of dielectric materials as a function of the reflection property of the material. Hence a relationship is mapped between the quality indicator of the pavement and the reflection coefficient of the radar. Secondly, road way samples of known quality can be directly measured by the radar system and correlated, thirdly, simulates of roadway materials such as dielectric composites or liquids are defined for direct measurement of the radar system and correlated to quality indicators of the pavement material such as density, moisture, stiffness or even modulus as described in U.S. Pat. No. 8,299,808.

Typical time domain pulse radars rely on network analysis to determine the reflection response or S11. However, Frequency Modulated ground penetrating radar system analysis may rely on electronic mixing technology whereby the incident and received signals are not divided, but are rather multiplied to find an intermittent or IF frequency response. This intermittent frequency response is further processed for quality indication of a roadway project.

While material measurements and material measurement improvement methods have been described in conjunction with network analysis and electronic mixing technology to determine parameters such as amplitude, impedance, permittivity, permeability, complex permittivity, and complex permeability by using S-parameters, it will be understood by those of ordinary skill in the art that other measurement systems utilizing other material analysis techniques may be used in conjunction with these methods and the device under test described herein. In fact, any electromagnetic wave analysis procedures that permit determinations of permittivity and complex permittivity either via software or manual methods may be implemented in conjunction with the present invention without departing form the spirit or scope of the claims.

With regard to FIG. 1, a ground penetrating radar system 100 is provided. Shown is a form of a bistatic system using a two antenna system. By incorporation of a circulator, this can be turned into a monostatic radar where a single antenna 102 both transmits and receives the pulse or frequency response. This antenna spaced apart from the surface with an air interface is known as air coupled, conversely, it can be in contact with the ground and ground coupled. By sampling the transmitted wave and the reflected wave, the reflection coefficient can be determined. For a perfectly smooth surface, the return waveform is stronger than for a rough surface. For surfaces that remain constant in roughness, the amplitude of the reflection waveform is related to the permittivity contrast between the air and pavement. In another embodiment, a heterodyne approach is of interest where the received signal is sampled and electronically mixed with a sample of the transmitted waveform. The nonlinear mixing results in an intermittent frequency of amplitude also related to the permittivity contrast and delay between the two signals With regard to FIG. 2, an air coupled single antenna impulse response is provided; shown are four (4) features in time. First is the reflection, A3, from the end of the antenna 200, whereas the second largest reflection feature 202 A1 is from the surface of the roadway. In this time domain approach, the amplitude of 202 is compared to the amplitude of 202 with a conducting plate and related to the permittivity of the pavement material, where permittivity is related to the quality indication.

Figure 2:
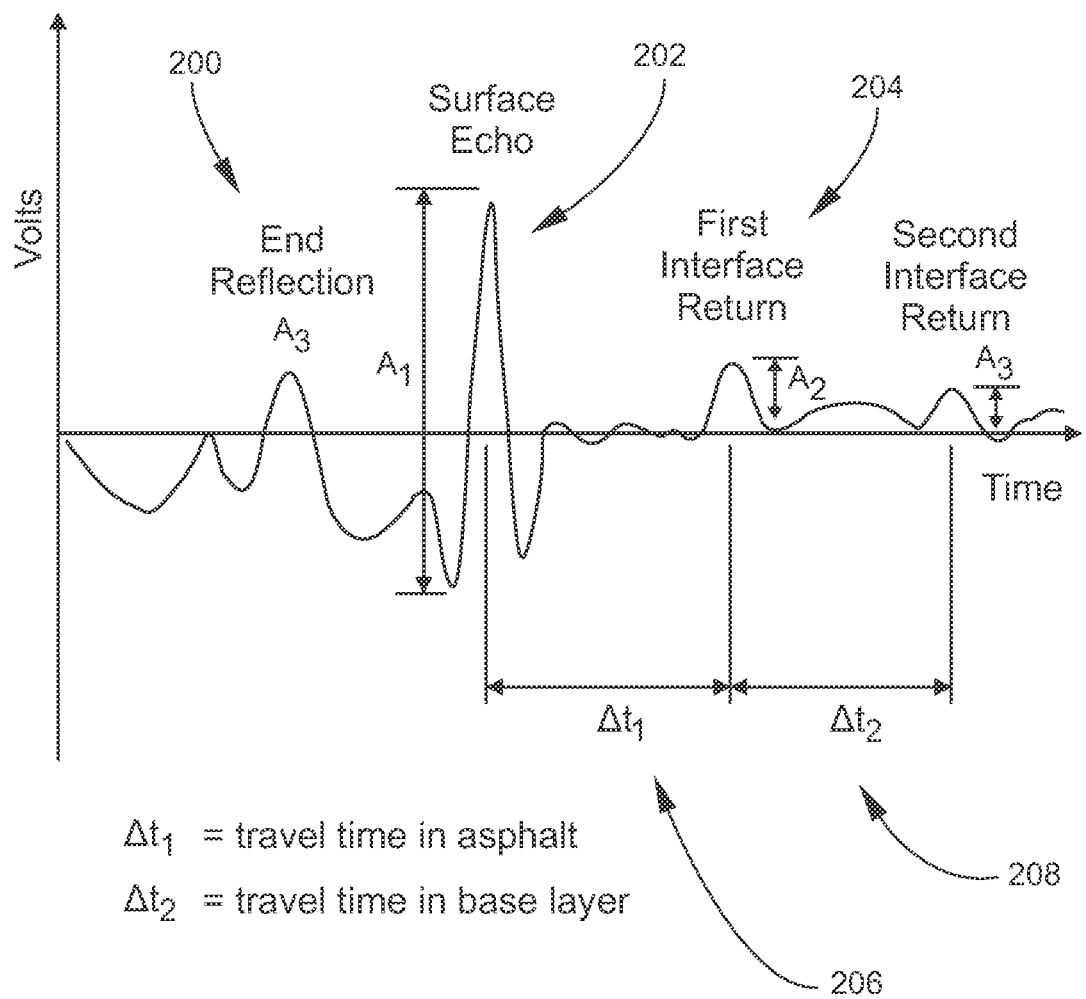
FIG. 2 is a block diagram showing an air coupled single antenna response where there are four (4) features identified in time.

There are several approaches historically for GPR investigations on roads. The early literature is based on pulse radar, where generally a 1 ns pulse is transmitted, and a reflection is recorded in the time domain. The largest reflection 202 from FIG. 2 is from the surface, the third and smaller reflection 204 is from the interface of the bottom of that surface layer and the next deeper layer. Using the time difference between the reflection peaks Delta $t_1$ 206 and Delta $t_2$ 208, the thickness of the asphalt may be determined if the dielectric constant of the roadway is known. If the dielectric constant is not known, a core may be drilled, and the thickness is physically measured, and the thickness physically measured is then calibrated into the system for the rest of the project.

In the asphalt pavement construction industry, the cylindrical asphalt core is a common sample geometry. In laboratories, cylindrical samples are prepared, typically with a gyratory compactor, and various material properties are studied to determine the best mix design for a pavement. In the field, cylindrical samples are cored from asphalt, concrete, soils, rock, test strips, newly constructed roads, or existing roads. The material properties of these samples are then used to evaluate whether the test strip or the new pavement meets the design criteria and whether an existing road is in good operating condition or in need of repairs. Among the material properties studied concerning the cylindrical asphalt samples, material bulk density or bulk specific gravity are important properties.

Accordingly, asphalt cylinders may advantageously be used in a resonant cavity to determine permittivity properties for calibration purposes. According to one embodiment of a method of determining the density of an asphalt sample, the permittivity analysis may yield density measurements. It may be noted that while a rectangular resonant cavity as described in U.S. Pat. No. 7,230,150 as an appropriate measurement device for an asphalt sample, other electromagnetic devices are known to those of ordinary skill in the art and may be substituted accordingly. For example, in calibration, transmission line analysis such as TDR as described by Topp, and structures and modes such as TEM, quasi-TEM, TE, TM. The measurements MAY be made in the reflection mode, transmission mode or combinations thereof. In any event, the electromagnetic radiation will interact in the near field with the material under test for contact devices, and possibly in the far field for non-contact devices. Here, the near field is typically defined as interaction or coupling close to the antenna, and is usually defined by distances<2 d/$\lambda$ where d is related to the dimension of the antenna, and $\lambda$ is the wavelength.

In order to obtain the density of asphalt, or the moisture content of a soil, a relationship or calibration must be found relating the permittivity and the property of interest. For HMA, one way is to compact samples of the pavement as a function of density, and measure the permittivity as a function of density in the laboratory. In the asphalt pavement construction industry, the cylindrical asphalt core is a common sample geometry. In laboratories, cylindrical samples are prepared, typically with a gyratory compactor, and various material properties are studied to determine the best mix design for a pavement. In the field, cylindrical samples are cored from soils, rock, test strips, newly constructed roads, or existing roads. The material properties of these samples are then used to evaluate whether the test strip or the new pavement meets the design criteria and whether an existing road is in good operating condition or in need of repairs. Among the material properties studied in the cylindrical asphalt samples, material bulk density or bulk specific gravity is an important property.

Accordingly, asphalt cylinders may advantageously be used in a resonant cavity to determine permittivity properties. According to one embodiment of a method of determining the density of an asphalt sample, the permittivity analysis may yield density measurements. It may be noted that while a rectangular resonant cavity is described below as an appropriate measurement device for an asphalt sample, other electromagnetic methods and devices are known to those of ordinary skill in the art and may be substituted accordingly.

Figure 3A:
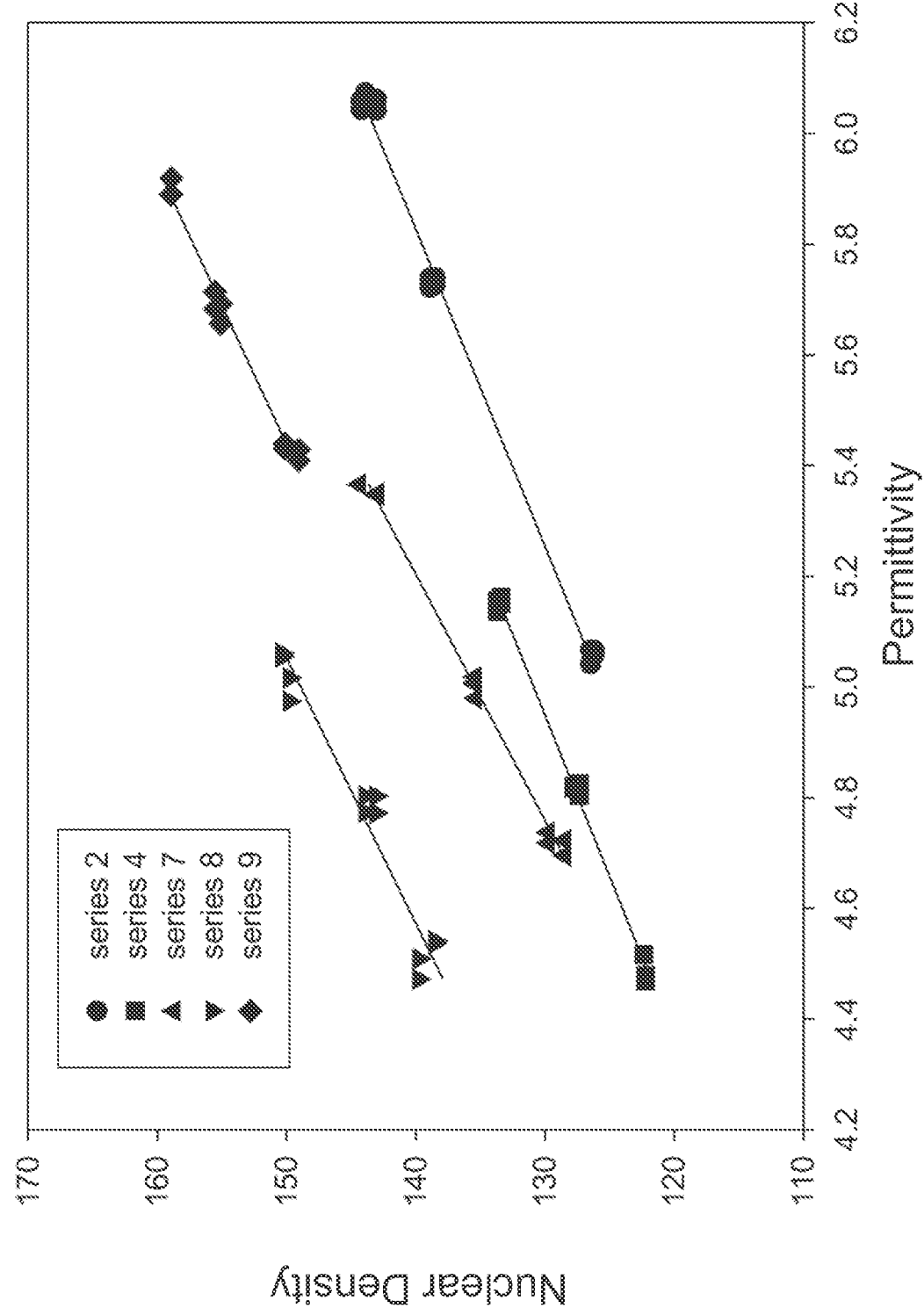
FIG. 3A is an example showing a plot, representing measurements of exemplary cores made from different aggregates and aggregate sizes, the data represents nuclear density vs permittivity.

With regard to FIG. 3A, as an example of a calibration process, consider the following core measurements. FIG. 3A represents measurements of exemplary cores made from different binders, aggregate species and aggregate shapes and sizes. These permittivities were measured using a resonant structure as described fully in U.S. Pat. No. 7,230,150. For the core 2-102, the resonant frequency response easily converts to a dielectric constant, and the results are shown in Table 2.

TABLE 2

| Freq | S21 | DeltaF | QL |
|---|---|---|---|
| X 368.5625 | −19.4509 | 0.72594 | 507.701 |
| O 368.3375 | −19.8601 | 0.76284 | 482.8496 |

| SampleID | Height mm | AVG | PCF(nuclear) | mass (g) | PCF (X) Microwave |
|---|---|---|---|---|---|
| 2-102 | 113.900 | 2.032 | 126.472 | 4102.9 | 126.291 |

| Freq | S21 | DeltaF | QL |
|---|---|---|---|
| 368.5625 | −19.4509 | 0.72594 | 507.701 |

| epsX | eppsX | fact | epsO | eppsO | fact |
|---|---|---|---|---|---|
| 5.00 | 0.039064 | 0.639827 | 5.028544 | 0.041223 | 0.638667 |

| CORE | er' | er" | PCF | slope | intercept |
|---|---|---|---|---|---|
| 2-102 | 5.042 | 0.039 | 126.472 | 17.444 | 38.340 |
| 0.000 | 5.067 | 0.041 | 126.472 | 0.367 | 2.088841 |
| 2-103 | 5.058 | 0.035 | 126.196 | 0.994 | 0.570606 |
| 0.000 | 5.067 | 0.039 | 126.196 | 2264.960 | 14.000 |
| 2-201 | 5.726 | 0.042 | 138.511 | 737.450 | 4.558272 |
| 0.000 | 5.740 | 0.047 | 138.511 | | |
| 2-202 | 5.725 | 0.040 | 138.911 | | |
| 0.000 | 5.728 | 0.042 | 138.911 | | |
| 2-203 | 5.722 | 0.043 | 138.929 | | |
| 0.000 | 5.739 | 0.040 | 138.929 | | |
| 2-301 | 6.060 | 0.038 | 144.228 | | |
| 0.000 | 6.043 | 0.036 | 144.228 | | |

TABLE 2-continued

| 2-303 | 6.042 | 0.040 | 143.019 |
|---|---|---|---|
| 0.000 | 6.062 | 0.042 | 143.019 |
| 2-305 | 6.074 | 0.042 | 143.890 |
| | 6.074 | 0.038 | 143.890 |

Using regression analysis, the slope and intercept of the permittivity vs. density have been calculated. $R^2$ is 0.994. Plots of the dielectric constant vs. density of the cores are shown in FIG. 3A. This figure shows that each mix may have a unique calibration for density; a consequence of the chemical composition, aggregate and binder type, aggregate orientation and shape and temperature of the mix. Temperature of the cavity is also very important as very small perturbations in the expansion or filling dielectric such as air effect the measured results. Temperature compensation of the sample and the measurement device are preferred.

Figure 3B:
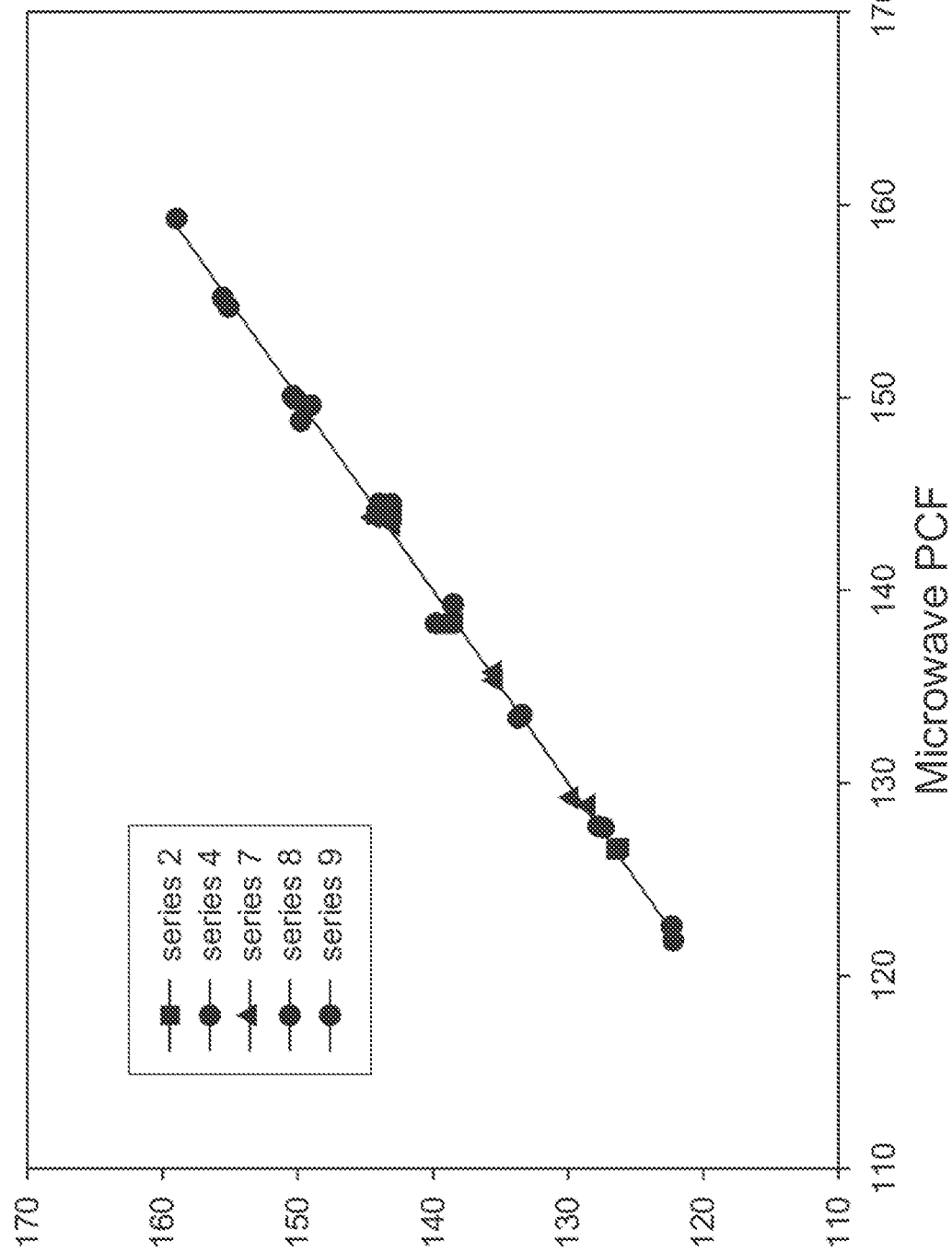
FIG. 3B is an example showing a plot of data representing nuclear PCF vs microwave PCF.

Once each mix has been calibrated, the microwave density of all samples were plotted vs. the nuclear density using a nuclear based core reader manufactured and patented by the inventor U.S. Pat. No. 6,492,641 as shown in FIG. 3B. It is important not to measure the samples in a water bath as the permittivity of water is 80 and water would fill the voids.

With regard to FIG. 3B, the standard deviation was 1.03 PCF. One sample Series 12 (not shown) had a difference of 4 PCF between the microwave method and the nuclear core method. Removing series 12 from the graph resulted in a standard deviation of 0.6 PCF. Mapping directly to permittivity is a good way to calibrate permittivity quality indicators, as then any method based on permittivity, whether a radar system or a fringing field capacitor system can be calibrated to permittivity and mapped to the permittivity—quality indicator database. Certain corrections or permutations to the permittivity "master curve" need to be considered with each measuring technology including frequency, frequency band, impulse width, depth of penetration, and surface scattering.

The laboratory measurements reported above in the calibration cavity were of the transmission type, and in particular measurements of S21. The measurements were obtained using a rectangular cavity with standing waves. The principle relationship between permittivity and quality indication are the same even if traveling wave type resonators are used, such as microstrip resonators or even antenna impedance techniques. These types of measurements may use the reflection techniques or $S_{11}$ as the measured value.

Although these mixes were made in the laboratory, the mixes produced at least one calibration curve as all the samples had similar slopes. This general curve, representing many different mixes may be offset in the field by comparing the radar measured density to a nuclear gauge density or a core density. Furthermore, for moisture, samples may be also be prepared in a laboratory setting and calibrations of the permittivity vs. moisture content performed. This can lead to a general curve which may be offset in the field using traditional moisture measuring techniques such as gravemetric methods incolving heating and weighing the soil, nuclear methods, other electromagnetic methods and the like.

The relationship for a plane wave striking the surface of a dielectric material, such as radar, can be related to density (or moisture) by a calibration process. By comparing the amplitude $A_m$ (or maximum peak) of a perfect reflector due to a metal calibration plate, to the reflection of the roadway $A_R$. The permittivity can be found using Equation 1 below:

$$\varepsilon_R = [(1+A_R/A_m)/(1-A_R/A_m)]^2 \qquad (1)$$

This permittivity $\varepsilon_R$ is related to the density of the asphalt layer through calibration curves such as shown in FIGS. 3A and 3B. Calibration can also be performed in the field, typically on a test strip where a nuclear gauge is used to measure the density and the value obtained by the non destructive nuclear gauge is used to offset a general calibration curve. Alternately, a series of GPR measurements and nuclear readings can be made for a full multi-parameter calibration curve fitting. Instead of using the Nuclear Density Gauge (NDG), cores can be drilled and density determined using the water bath system such as AASHTO T166-07 or alternative method. In Equation (1), $A_m$ is a response where a metal plate is used to find the largest possibly reflection peak. This simple instrument calibration technique aids in removing systematic error from the system. Other methods would incorporate comparing the pavement reflection $A_R/A_m$ instead to the common end ringing of the antenna, or a lumped element known load integrated into the radar circuitry, or to a non conducting calibration plate of predetermined permittivity. This permittivity may be on the order of $\varepsilon=10$.

One issue with using a radar pulse method in the time domain is for typical road thickness, a ground coupled antenna has a return signature that takes place before the ringing of the antenna and system has settled down from the transmission of the pulse. In other words, it is hard to pick out and resolve time domain peaks because of the inherent resolution, unless the antenna is relatively far from the surface, or the pulse is narrow and the antenna is of extreme bandwidth such that the return signature is clearly observable and resolvable. Even without the ringing of the antenna, when the features are close as in these thin layers, it is difficult to resolve the surface and bottom layer features, or even the primary surface reflection. This leads to uncertainty and error in determining the dielectric property or quality indication of a thin top layer 1 to 4 inches thick.

For this reason, a frequency domain radar or FMCW system is proposed whereby the processing takes place on an intermittent frequency or IF, and the sweep rate, and bandwidth determine the resolution. Furthermore, by filtering the frequency data, information of different depths or layers can be determined. Additionally, by choosing higher frequency sweeps, the losses in the pavement material can also determine the depth of penetration of the electromagnetic energy. One such layer selective method incorporates skin depth penetration, another layer selective method incorporates frequency filtering of the data selecting higher frequency content with a band pass or band stop filter, a third layer selective method incorporates exciting surface waves whereby the electromagnetic energy penetrates deep for lower frequencies, and close to the thin top layer for the higher frequencies. Non-limiting exemplary frequencies for asphalt may be from 1 GHz to 2 GHz to approximately 10 GHz or even as high as 20 GHz. For soil moisture measurements, non-limiting exemplary frequencies may range from 300 MHz to several GHz is appropriate. If the bandwidth is at least 25% of the center frequency, the system may be considered as ultra wide band UWB. For example, sweeping from 1.5 to 2.5 GHz would constitute an UWB FMCW. Wide bands are desirable for resolution and in some cases depth control.

Figure 4:
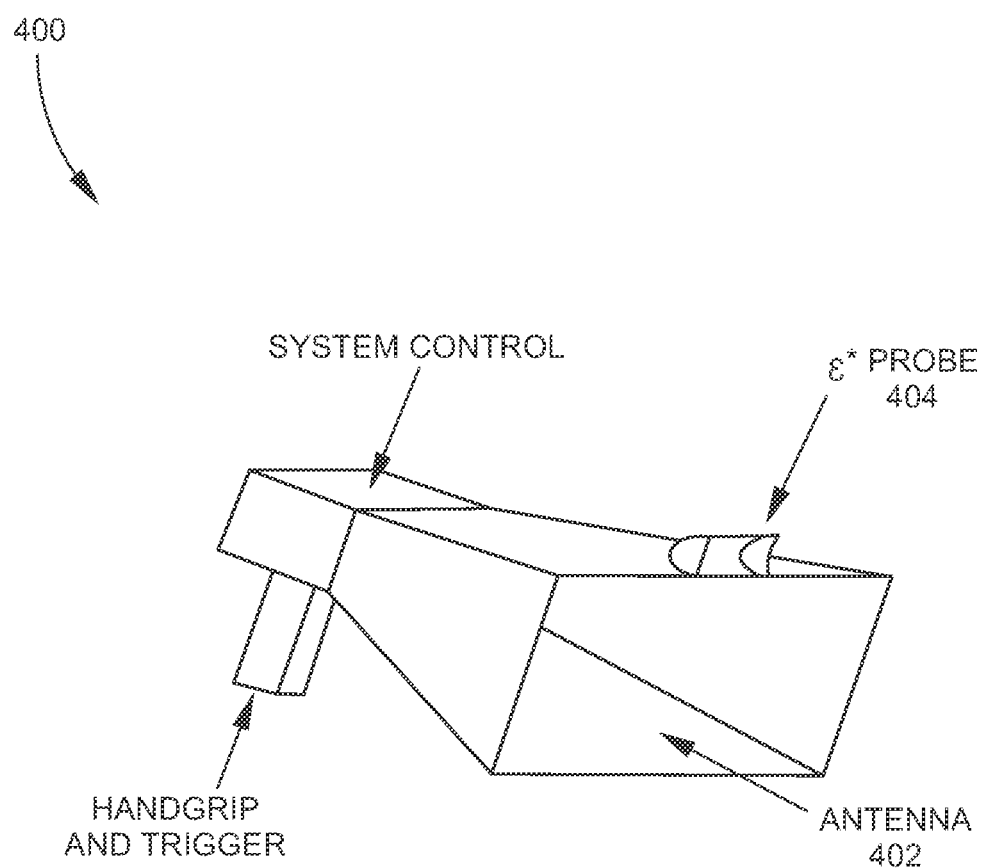
FIG. 4 is an example conceptual drawing showing a handheld radar system.

With regard to FIG. 4, when determining the thickness of asphalt or a pavement material using GPR the permittivity of the underlying material is often unknown. The user then obtains the actual core thickness by drilling, and calibrates the GPR system to that core thickness or calculates the permittivity from the timing diagram results and the known thickness. FIG. 4 shows a ground penetrating radar system 400. The ground penetrating radar system 400 is comprised of an antenna 402, a relative permittivity $\varepsilon_R$ probe 404 and a trigger to initiate the measurements. The ground penetrating radar system 400 further comprises a system control 406 for controlling the permittivity measurements and the radar transmissions. The antenna 402 may be configured for measurements in either the time domain (TD) or the frequency domain as in FMCW. The relative permittivity $\varepsilon_R$ probe 404 may be mounted directly on the antenna 402 or couple separately, for example, mounted on a carrying frame such as a vehicle or held by hand directly on or in communication with the ground penetrating radar system 400. FIG. 4 shows a ground penetrating radar system 400, wherein the frequency of interest in the band of the GPR is used to probe 404 the pavement material to obtain the permittivity characteristics. This permittivity probe 404 is calibrated in the factory on standards of known dielectric properties. A calibration curve is then obtained for the permittivity probe 404, for finding the true permittivity and thus phase velocity $v_p$ of the pavement material. Then the thickness is determined by calculation based on the timing in the reflection measurement and $v_p$. Because of the issues surrounding a pulse radar system, a frequency domain radar or FMCW system is proposed optionally in conjunction with the probe 404 whereby the processing takes place on an intermittent frequency or IF, and the sweep rate, and bandwidth determine the resolution.

Figure 5A:
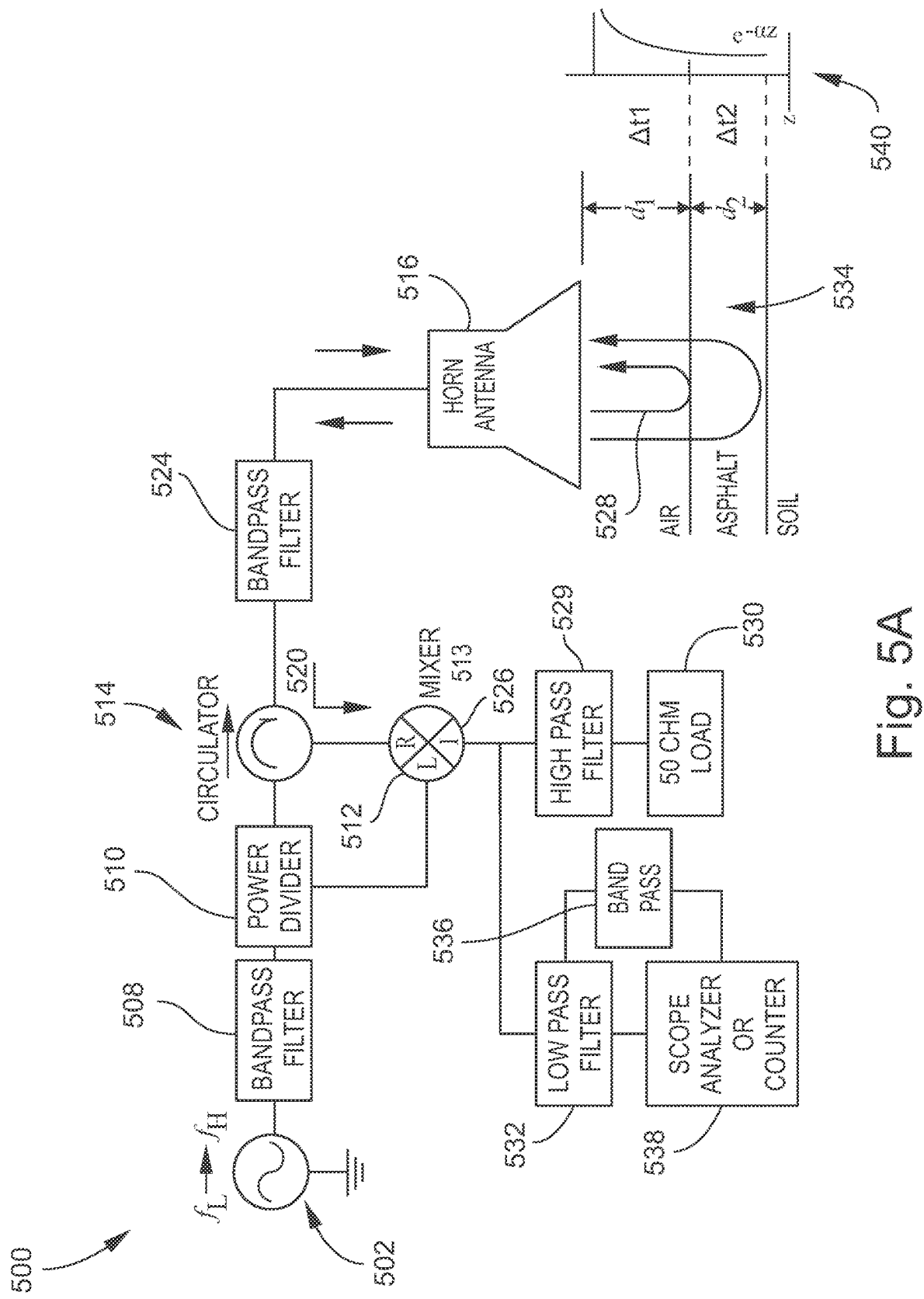
FIG. 5A is a block diagram showing the system control and antenna of the ground penetrating radar system.

With regard to FIGS. 5A and 5B, a FMCW radar system 500 which incorporates a sweeping frequency generator 502 to produce the microwave radiation is shown. The frequency generator 502 is a voltage controlled oscillator (VCO) controlled by a sawtooth or triangular waveform as shown in 504 in FIG. 5B.

With regard to FIG. 5, a block diagram of an exemplary FMCW system is shown. It may be noted that the components described are for exemplary purposes. An HP 62368 DC power supply (not shown) provides 5 V to the Mini-Circuits JTOS-3000 VCO 502. A function generator (not shown) provided the VCO modulation signal 504 of FIG. 5B, a 100 Hz triangle wave from 0 V to 10 V, producing a VCO output 505 frequency ranging from 2000 MHz to 3475 MHz (approximately) 506 at a power level of between 5.5 mW and 8.5 mW. The VCO output 505 was fed to a filter 508 and then to Narda model 300310 10 dB directional coupler or power divider 510. The 10 dB output was provided directly to the LO input 512 of a Remec-Magnum model MC17P-4 mixer 513. The other output was provided to port 1 of a Western Microwave model 3JA2040 circulator 514. The forward output of the circulator (port 2) was then coupled to an American Electronic Labs model H5101 horn antenna 516, designed to operate with an antenna gain of approximately 15 dB over the frequency range from 2 GHz to 5 GHz, as an example. The reverse output of the circulator (port 3) was connected to the RF input 518 of the mixer 513. The mixer 513 multiplies the LO input 512 and the RF input 518 513 producing a downconverted frequency, the difference in frequency between the LO input at 512 and the RF input 518 from the target return signal 520, and a high frequency component the sum of these two frequencies. Similar to a superhetrodyne receiver.

In FIG. 5B, the transmitted signal 522 is occurring at t=0 and is the microwave frequency ωo with amplitude A1 and frequency $F_L$. Being a time harmonic signal this is represented by the microwave signal A1*Cos(ωot). This harmonic signal is split at the power divider 510 and provided as the LO input 512. Simultaneously the microwave signal of frequency ωo is transferred though the circulator 514 and filtered 524 of any harmonics and noise and sent to antenna 516 where it is propagated through air and hits the surface of the pavement material.

This is reflected back to the antenna 516 and through the reciprocal filter 524 with a time delay of 2Δt1. This is defined from the oscillator circuit 5B where the sawtooth or triangle wave response 504 has moved the LO 512 to ω1 with amplitude A2 and frequency $F_H$ resulting in RF energy A2*Cos(ω1t). The ideal mixer then produces the sum and difference frequencies by the identity $$V\text{out}=A1*\text{Cos}(\omega ot)*A2*\text{Cos}(\omega 1t)=(A1*A2)/2*[\text{Cos}(\omega 1-\omega o)t+\text{Cos}(\omega 1+\omega o)t]$$

which appears at the output port 526 of the mixer 513.

The amplitude A2 resulting from a reflected wave 528 off the pavement is the result of the air dielectric interface. For example, if the relative dielectric constant of the pavement is ε2 then the amplitude related to A2 of the reflected wave 528 is the magnitude of $S11=(1-\sqrt{\varepsilon 2})/(1+\sqrt{\varepsilon 2})$. As the moisture and density increases, the magnitude of A2 increases. Since the amplitude of the FMCW is really a composition of the mixed signals, Equation 1 is interpreted as AR=A1*A2.

The output signal 526 of the mixer 513 containing at least two composite frequency components $F_H-F_L$ and $F_H+F_L$ is then separated. At this point a high speed ADC can be used to digitize the composite signal whereby digital filters and techniques can be used to separate and operate on the signals, or the high frequency $F_H+F_L$ component can be filtered by an analog high pass filter 529 and provided to a 50Ω load 530. The low pass filter 532 is used to separate out the down converted signal $IF=F_H-F_L$. The filter 532 may be defined as a passive or lumped element microstrip filter such as a Butterworth filter or Chebyschev filter or the like.

Figure 8A:
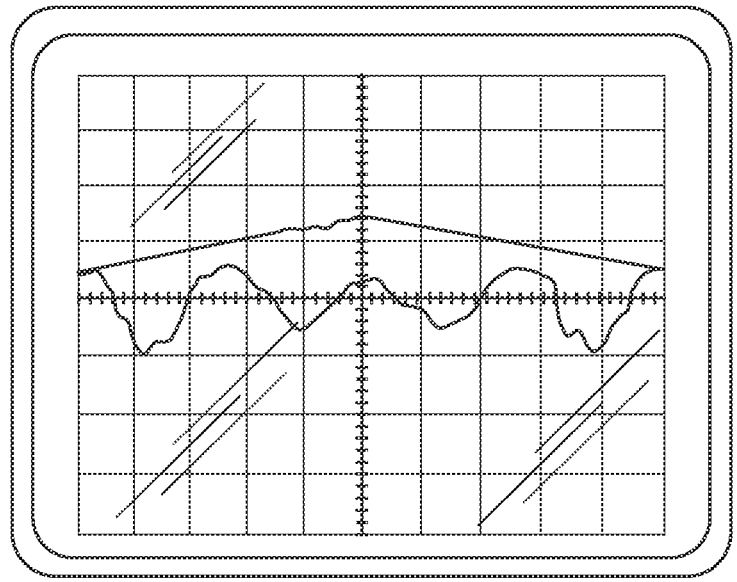
FIGS. 8A and 8B are a graph of scope plots showing the differences between the reflected IF signal responses received by the radar system.
Figure 8B:
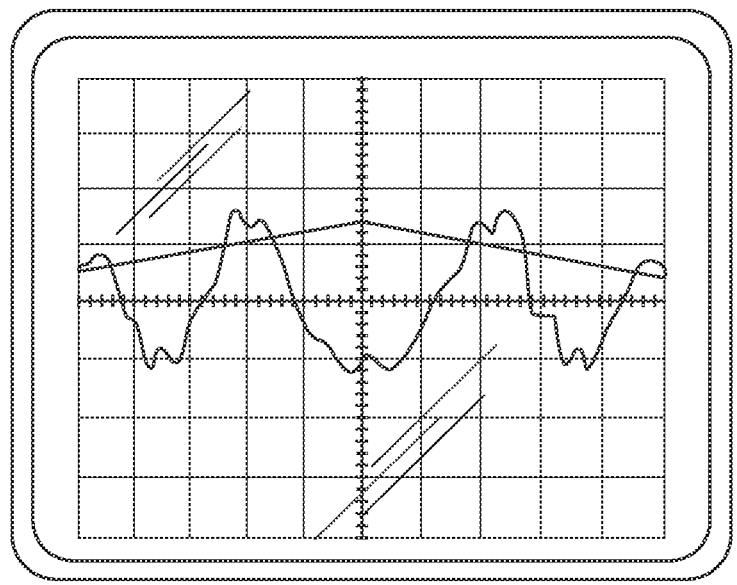

In this example, of interest are the surface properties. Hence, to select the surface reflection the lowest frequency in the IF is of interest. This lower frequency is represented by FIG. 8B, which has the largest amplitude as similar to 202 of FIG. 2. Note that the filtering is not perfect, and that there are higher order components present in FIG. 8B. The higher order frequency components represent signals that are reflected off a deeper layer such as d2 534 as shown in FIG. 5A. Reflected signal off a deeper layer d2 534 would have a longer delay, namely 2(Δt₁+Δt₂) and the "beat" frequency from the mixer is thus much higher as defined by FIG. 5B and ω2−ωo. Hence, in order to extract the information from deeper layers such as thickness, a second band pass filter 536 can be added. For multilayer information multiple filtering and processing, the properties of layered media may be directly measured.

The LF output 538 of the mixer 513 was observed on a Tektronix model 2465A oscilloscope acting as the analyzer 538, with the second scope trace showing the VCO modulation signal. The oscilloscope output for a pavement surface of distance of approximately ten (10) inches away is shown in FIG. 8A and described below. The oscilloscope plot for a pavement surface distance of approximately four (4) inches is shown in FIG. 8B. These results are also similar to the response of a pavement material of two layers of different permittivities 4 and 6 inches thick.

With these experimental parameters, the expected low or intermediate frequency (IF) as a function of sweep rate R and distance d1 to the reflecting surface in air is $$f_{IF}=(2Rd1/c)$$

or $$d1=f_{IF}/2Rc$$

For example, in FIG. 5B, with c=3×10⁸ m/s in air and R=295×10⁹ Hz/sec (1020) (i.e., $f_H-f_L$=1475 MHz 506 and T=0.005 sec 505), the measured intermediate frequency for d1=4 inches is $f_{IF}$=200 Hz, and for d1=10 inches $f_{IF}$=500 Hz.

The circuit shown in FIG. 5A (no see) can be used with a commercial programmable DSP chip such as those available from TI, Motorola, or Analog Devices to perform frequency analysis of the LF output using sampled A/D conversion with a discrete FFT algorithm. Many DSP vendors sell chips that are optimized for the FFT priced depending primarily on floating point capability and clock speed. Because the bench prototype FMCW produces a low output frequency, clock speed may not be a driving issue for DSP selection unless operations are performed before filtering where the microwave band exists. Floating point capability would simplify algorithm development. However, since the output signal is quite predictable, most of the mathematical calculations may be done off-line and only the final numerical solution and conversion to a readable output may be performed on-chip.

Before DSP hardware and software is developed, the RF circuitry may be optimized and miniaturized. The benchtop components may be replaced with surface mount components on a single circuit board, which may be mounted on the back of the horn antenna or other antenna such as an Ultra Wide Band, bowtie, dipole, conical, spirals, and loaded antennas may also be used. Appropriate filters must be added to the output to select the desired frequency range. A power budget must be created to verify that the output power level is sufficient to produce an adequate signal to noise ratio in the fielded system. In other words, system losses and anticipated losses in the propagation of microwaves in a moist construction material may be considered along with the typical radar range equations to make sure a few mW is all that is necessary from generator 502.

FIG. 5 shows the antenna 516 reflecting off the pavement material surface and penetrating into the material. For moist materials such as soil, there is an attenuation factor related to the frequency of operation, conductivity of the material, and various losses-relaxations exhibited in the complex permittivity. This manifests itself in the exponential attenuation function of coefficient α(ω) illustrated in 540. As the attenuation in moist substances or lossy asphalt is stronger at higher frequencies, proper selection of the frequency of operation or bandwidth can act to limit penetration as α(ω) increases with frequency. Hence thin surface layers can selectively be measured with higher frequencies. For FMCW, FIG. 5C 542 shows a VCO sweep from the VCO 502 where the frequency content is 5 Ghz to 10 Ghz, as an example. Selecting these sweeping parameters can limit the depth of penetration.

Figure 6:
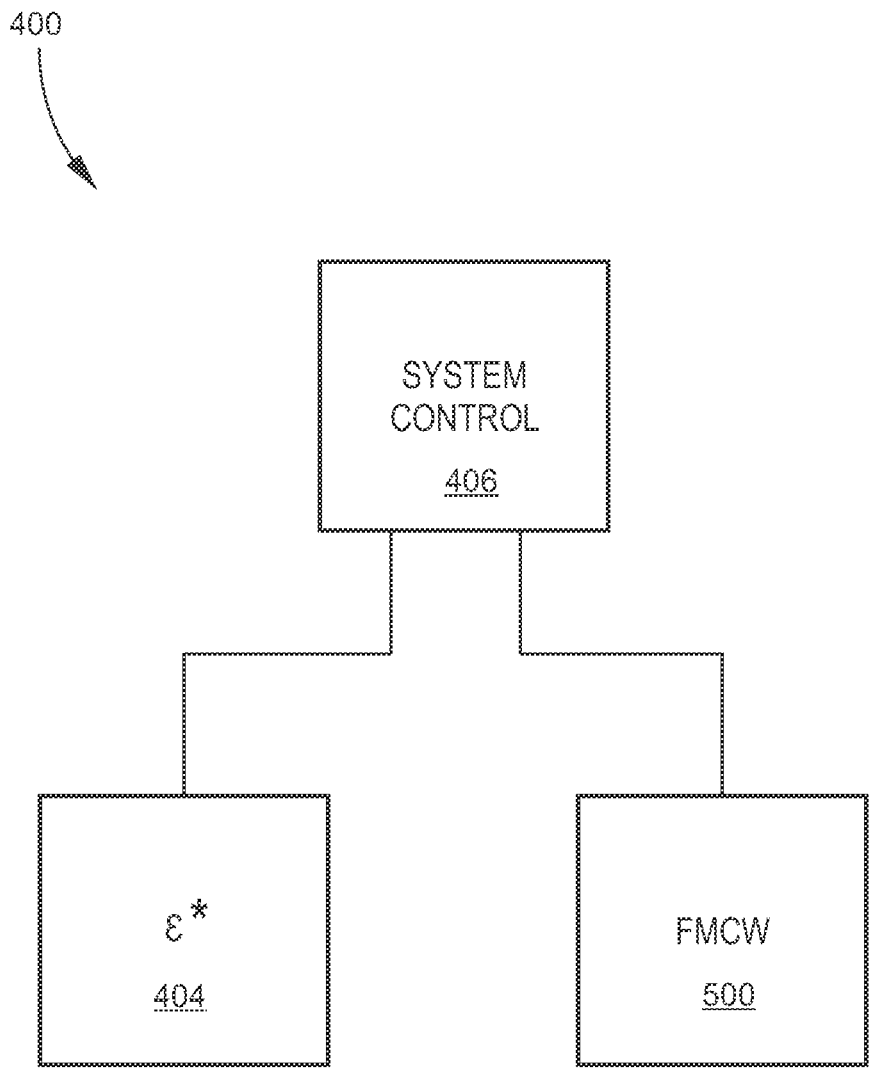
FIG. 6 is block diagram showing a system controller coupled to the permittivity probe and the FMCW radar system.

With regard to FIG. 6, is a block diagram showing the ground penetrating radar system 400 comprising the permittivity probe 404, an antenna 516 configured for FMCW transmissions and measurements and the system control 406. The system control 406 is configured to coordinate both the permittivity measurements and the FMCW transmissions. Based on the permittivity measurements which are correlated with the recorded calibration, data a dielectric constant is thus calculated. This calculated dielectric constant is used to calculate transmission signal velocity in the tested material. Using the transmission signal velocity a depth of material is then determined.

Figure 7:
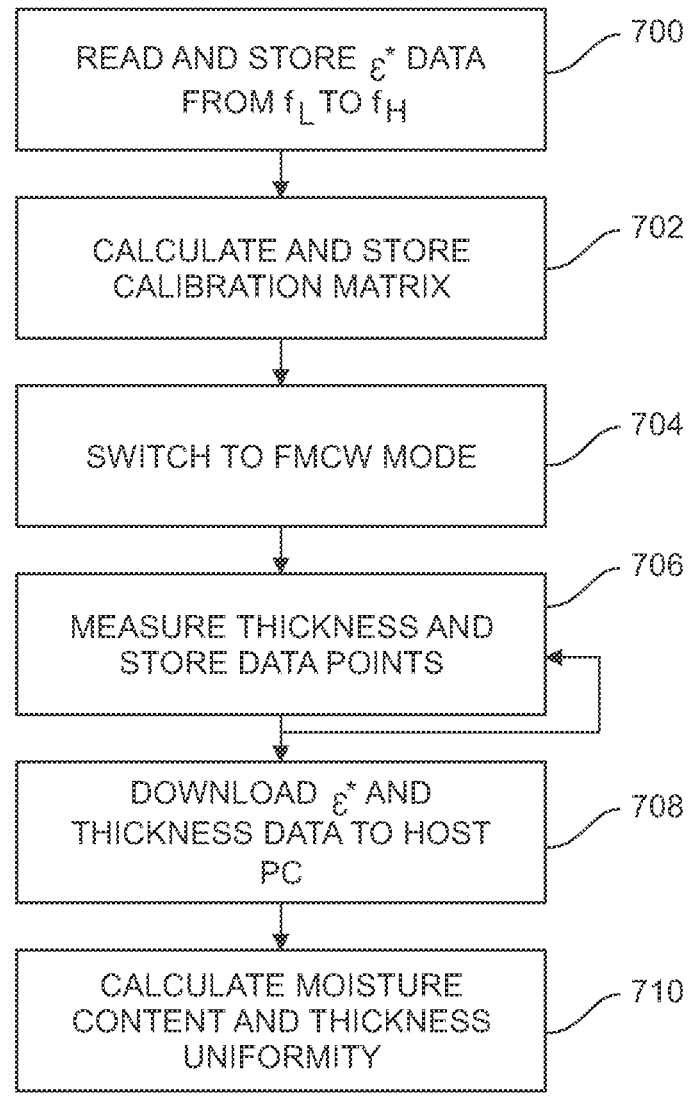
FIG. 7 is a flowchart showing a sample process of obtaining permittivity data, switching to FMCW mode, measuring thickness and storing data for downloading to the host PC.

With regard to FIG. 7, a flow chart showing the process for capturing and coordinating both the permittivity measurements and the FMCW transmissions by the ground penetrating radar system 400. In block 700 the ground penetrating radar system 400 will read and store the permittivity ε data from the frequencies $f_L$ to $f_H$. The frequencies $f_L$ to $f_H$ may be determined based on the expected depth measurements, HMA mix parameters, and expected moisture content of the material and/or the soil, as non-limiting examples. The ground penetrating radar system 400 then calculates and stores calibration matrix data (block 702). The calibration matrix data will be used to compensate for various material properties and system errors introduced by the ground penetrating radar system 400. In block 704, the ground penetrating radar system 400 may be switched to FMCW mode for making the thickness measurements.

Alternatively, in block 704, the ground penetrating radar system 400 may be switched into a moisture mode or an asphalt mode. The moisture mode is used for making moisture measurements on soils and/or sub bases based on the dielectric constant measurements. Further, the ground penetrating radar system 400 may be switched into various material modes, such as asphalt or roller compacted concrete mode, as non-limiting examples. The various modes will alter system parameters, such as frequencies $f_L$ to $f_H$, signal transmission strength, and number of sample data points as non-limiting examples. Next the ground penetrating radar system 400 measures thickness and stores data points (block 706). The number of measurements and data points measured and stored is dependent on the system mode selected. With continued reference to FIG. 7, the permittivity ε data measured from frequencies $f_L$ to $f_H$ in block 700 and the thickness data measured in block 706 is downloaded and stored in the host PC or computer (block 708). Once downloaded the ground penetrating radar system 400 can calculate moisture content and thickness uniformity as disclosed herein. This may be implemented as an embedded system.

With regard to FIGS. 8A and 8B, the mixed down IF intermittent frequency responses from two different thicknesses of material are shown. The ground penetrating radar system 400 operates by the microwave voltage controlled oscillator (VCO) 500 ramping in frequency. The ramp in frequency can be from one (1) GHz to two (2) GHz, as a non-limiting example. The ramp in frequency may be controlled with a sawtooth pattern and is simultaneously sampled and provided to the mixer 513 and transmitted by the antenna 516, in this example it is a horn antenna. So the antenna 516 is transmitting a continuous wave (CW) signal at any time the frequency changes with time. The amplitude of the voltage controlled signal 505 remains constant. There is a time delay between when the voltage controlled signal is transmitted and when the voltage controlled signal is received. The time delay correlates to the thickness of the material 534. During this time delay, the transmitting antenna 516 has changed frequency by the sweep rate, so by the time the return frequency has been sampled, it is of a lower frequency ($f_1$) than what is being currently transmitted ($f_2$). The circulator 514 separates these transmitted and received signals. The mixer 529 mixes the transmitted and the delayed received signals and produces a spectrum of two frequencies 526. One component is the sum of the frequencies transmitted and received and one component is the difference of the frequencies. The actual mixed result from two frequencies may be A cos(w1*t)*B cos(w2*t) is =AB cos[(w2−w1)*t]+AB cos[(w2+w1)*t]+DC components. In this example, a voltage controlled signal is transmitted at a frequency range of one (1) to two (2) Ghz and the IF results from the mixer are approximately 500 Hz to 1.5 KHz. The low frequency component $f_{low}=f_2-f_1$ is filtered out and shown on FIGS. 8A and 8B. The high frequency sideband may be filtered 529 and may be terminated into the 50 ohm load 530, such that reflected and subsequent interference is minimized.

With continued reference to FIGS. 8A and 8B, the thickness of the material under test 534 will correlate to the amplitude of the reflection based on the attenuation of the reflected voltage controlled signal. For example, as shown in FIG. 8B, if the thickness of the material under test 534 is four (4") inches, the voltage controlled signal will have to propagate less, thus the reflection will have a larger amplitude due to less attenuation of the voltage controlled signal. In this example, if the material under test 534 is thinner, 4" for example, then the VCO will not have changed much in frequency between the transmitted voltage controlled signal and the received signal 520. Thus, the difference in frequency ($f_2-f_1$) will be smaller. As an additional example, as shown in FIG. 8A, if the material under test 534 is ten (10") inches, thicker than the 4" in the above example, the difference in frequency ($f_2-f_1$) is much greater. This is because the propagation and subsequent attenuation of the voltage controlled signal is greater. Thus, the amplitude is less as it has had greater attenuation. As may be noted in the individual waveforms other frequencies are superimposed on the IF. The superimposed individual waveforms of other frequencies are due to greater depths with greater frequency differentials that have been summed on the wave. The unwanted waveforms of other frequencies may be filtered out and separated using the filters as shown in FIG. 5A.

With continued reference to FIGS. 8A and 8B, density measurements may also be acquired. For density measurements, the antenna-surface distance will remain the same. In this manner, the frequency in FIGS. 8A and 8B will not be different because the height of the antenna 516 is constant above the ground, in this example. However, in the density mode it will be observed that the difference in amplitude of the reflected or received signal from one location to another will be different based on a change in the density. If the density goes up the amplitude of the reflected signal is greater, based on the increased or decreased dielectric constant.

In thickness mode, the reflection response is mixed with the transmitted voltage controlled signal 526 and the frequency increases as a function of thickness. For density mode, as long as the distance from the antenna 516 to the pavement surface is constant, the frequency will be constant, and the density will be related to the amplitude as described in Equation 1. With a FMCW, the electronic processing is performed at an IF much less than the microwave transmitted wave, and allows for lower cost, less complicated electronics and analysis. Additionally, the GPR as disclosed may also be based on a time domain modulated pulse signal.

In the microwave region, the temperature effects of polar molecules are relatively small. However there will be temperature effects due to the simple volume expansion of the material under test. This is because the method of measurement is based on the dipole moment per unit volume of material. In this respect, temperature corrections to the microwave results may be useful for the most accurate results in quality assurance of paving materials. These linear corrections may be related to the base temperature of the asphalt. For instance, this expansion is confirmed by the ASTM standards committee. See "Standard Practice for Determining Asphalt Volume Correction to a Base Temperature" D 4311-96. The preferred method of temperature measurement incorporates the use of an infrared device for noncontact IR temperature reading. Since density is related to volume, this correction factor based on temperature is used to correct for density measurements in HMA.

Surface roughness indicator/corrector operate at duel frequency bands; a first measurement is significantly higher in frequency while the second measurement is at a significantly longer wavelength. The principle here is at the shorter wavelengths, the scattering from surface voids is greater than with the longer wavelengths. The smoother the surface the larger the amplitude of the high frequency return loss. Exemplary higher frequencies would be 6-10 GHz to 20 GHz bands. Exemplary lower frequency bands would be 1 Ghz to 2 Ghz. In practice, analyzing ratios of the permittivity response in these two different bands results in, the correlation between the two bands increasing with a smoother roughness. Suppose the return loss for the high frequency response is $\Gamma_H$, while the lower frequency response is $\Gamma_L$. It is contemplated that $\Gamma_H < \Gamma_L$ for rough surfaces, and $\Gamma_H/\Gamma_L$ or $\Gamma_H(\omega)/\Gamma_L(\omega)$ increases towards 1 for smooth surfaces, and is less than 1 for rougher surfaces. For asphalt, the procedure is to obtain the asphalt density using the lower frequency band and find $\Gamma_L$. Use $\Gamma_L$ in Equation 1 along with the calibration to calculate the density $\rho$. Use the high frequency scattering measurement $\Gamma_H$ to find the correlation between the low and high reflection coefficients. If the surface is perfectly smooth, then the coefficient is 1 and no correction is necessary. If the surface is rough, then $\Gamma H/\Gamma L$ may equal 0.75 and the correction is:

Density=$\rho$+8.33*(1-$\Gamma H/\Gamma L$)=$\rho$+2.08 PCF

And the density has been corrected by adding 2.08 Lbs/ft3 to account for the surface scattering. The value 8.33 and the intercept may be found by averaging over several days on a project. This particular correction factor limits the roughness correction to 5 PCF. Other methods ratio the low and high frequency responses and weight the ratio towards a calibrated correction factor in density. Surface roughness and calibration techniques are discussed in U.S. Pat. No. 7,239,150 filed in October 2003 included here in its entirety.

Additionally, FMCW radars such as presently described are used for inspecting the quality control of pavement materials such as asphalt, aggregates and soils. In one example, FMCW radars are incorporated into hand held units for spot checking of thickness, density, moisture content. In another example, radars can be attached to pavement compactors such as conventional compactors, and intelligent compactors. Here information can be transferred to the operator or to a server data base for further analysis. Examples of density and moisture quality control devices attached to compactors can be found in Troxler U.S. Pat. Nos. 4,979,197 and 5,029,194. Further, as to the quality of pavement compactors are conveyor bins carrying aggregates in concrete plants and asphalt plants. Here, not only is asphalt and cement content of interest, but most importantly the moisture content of the sand and aggregates can be measured and recorded in a non-contact fashion, in real time if desired.

Probably the most important bit of information when building a road or infrastructure is the moisture content of the material. For the proper compaction of any soil, optimum moisture content is very important. Probably more important than the actual density, as the optimum moisture is achieved throughout the project, the maximum density is always obtained, and obtained in the least amount of time, by proper applied compaction energy. In other words, if a predetermined optimum moisture content and rolling compaction setup is used, a minimum number of passes will all but guarantee target density. Hence, one purpose of this invention is to integrate both asphalt density and soil moisture content directly into a ground penetrating radar system 400 for quality control of pavement materials. Hence, a single radar device can be used for all platforms with the simple choice of the calibration routines. A compactor that has a radar system compatible with many different materials is desirable. The ground penetrating radar system 400 may be used for this purpose. Applications for intelligent compaction include continuous compaction control (CCC) constantly imputing intelligent compaction measurement values (ICMV). Positioning systems such as GPS and dead reckoning using accelerometer and velocity as a function of the radar measurement may also be sent to the data base. Temperature from IR radiation sensors is used to correct the density and moisture as fully described in U.S. Pat. No. 7,230,150.

The principle for obtaining the soil water content with an air coupled radar is similar to the asphalt density as described in Equation 1 where the reflection coefficient in general is $S_{11}=(1-\sqrt{\varepsilon_{soil}})/(1+\sqrt{\varepsilon_{soil}})$ As in the asphalt case described above, the reflection coefficient is determined from the measured amplitude of the radar return. To calibrate the system, typically a metal plate is used to compare and calibrate the reflection to the bare soil reflection. The metal plate can be sufficiently large and of shape to reflect a maximum signal to the receiver, minimizing edge and corner effects. Other methods of calibration include measurement of the antenna mismatch, or incorporating loads internal to the system of sufficient impedance and delay or phase to simulate or compare to a radar reflection. Such impedances include loads such as delay lines, opens, shorts, complex and real impedances.

Surface roughness and profiles of water as a function of depth allow the opportunity for correction to obtain more accurate results. These can cause significant scattering which leads to a decrease in the measured permittivity; thus lower density or quality value for asphalt, or a dryer soil estimate for sub bases. Using the Rayleigh criterion, surfaces<⅛$\lambda$ may be considered smooth. As an example, this may be 38 mm for a 1 GHz antenna, and 0.167 m for 225 MHz in the VHF band just below the UHF. Surface roughness and water depth profiles are key issues that need to be addressed. By analyzing pavement materials using multi-frequency analysis, the depth of penetration can be selected by proper frequency depending on the skin depth of the pavement material, and the surface roughness can be assessed using a multi frequency technique.

The present invention also provides an apparatus and method for dynamically measuring the density of asphaltic material, moisture of soil, and the quality indicators of pavement materials during the process of compaction. The gauge includes a non-nuclear radar source and a radar receiver means which can be mounted in spaced relation from the surface of the test material to form an air gap there between, or be directly coupled to the ground.

Figure 9:
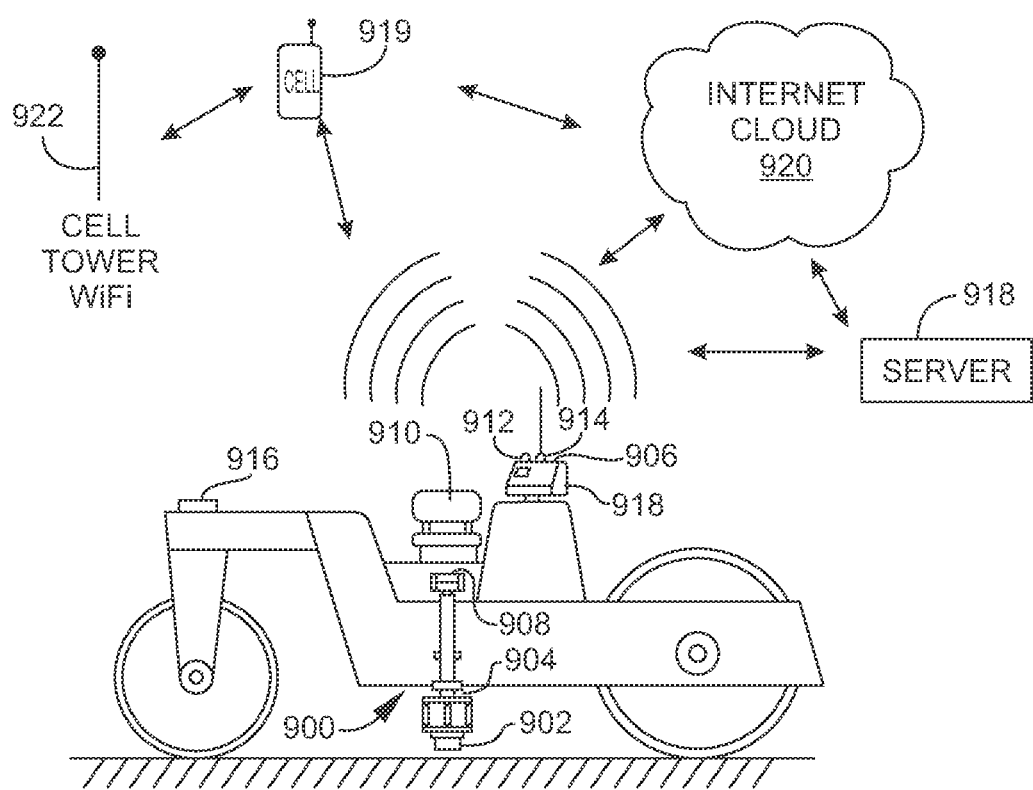
FIG. 9 is a diagram of a roller compactor or intelligent compactor configured for the radar system and wireless communication with various electronic devices for storage of measurement data and/or control of measurement readings.

FIG. 9 shows a compactor of the classical type or an Intellectual compaction device outfitted with a FMCW radar system 900 for measuring the compaction quality of asphalt, or the moisture content of soil beneath the compacting device. The radar system consists of at least one antenna 902 for transmitting and receiving microwave signals. Microwave circuitry components and modules are contained in packaging 904 and transmitted to display 906 via wire or wirelessly at 906. Operator controls compactor from position 910 allowing observation of display 906. During the construction of roadways, the contractor is required to obtain certain target densities, moduli, and moisture contents. By observing alarms in display such as an audible alarm or a visual light alarm in 912, the operator knows when target has been reached or if progress is being made. This display may be a bar graph showing changing roadway conditions as the compaction is in progress.

During construction of roadway sub bases and soil embankments, proper density and modulus cannot be achieved easily, or at all if the moisture is not within some percent of optimum value. If moisture of the soil is out of range, an alarm indicating so is localized through 912, and data is transmitted to foremen wirelessly through antenna 914. Real time data from the radar system 900 in conjunction with real time IC data such as project location via GPS 916 can be wirelessly relayed to the site server 918, individual computer devices such as cell phones and computer pads 919, and the Internet cloud 920. Wireless technology 922 such as CDMA, GSM, BLUETOOTH®, or common RF links such as IEEE 802.11 are incorporated. Data from the radar and IC links can also be stored on mobile computer 918 directly on the compactor.

The air gap between the antenna and the pavement material beneath the compactor remains substantially constant. Variations must be corrected for as this distance affects the amplitude of the reflected signal. Typical calibration routines are similar to the hand held unit, such as relating to lab samples and comparing the actual measurements to the reflection off the surface of a metal or dielectric plate.

Many modifications and other embodiments of the present disclosure set forth herein will come to mind to one skilled in the art to which the present disclosed subject matter pertains having the benefit of the teachings presented in the foregoing descriptions and the associated drawings. Therefore, it is to be understood that the present subject matter is not to be limited to the specific embodiments disclosed and that modifications and other embodiments are intended to be included within the scope of the appended claims. Although specific terms are employed herein, they are used in a generic and descriptive sense only and not for purposes of limitation.

It will be understood that various details of the presently disclosed subject matter may be changed without departing from the scope of the presently disclosed subject matter. Furthermore, the foregoing description is for the purpose of illustration only, and not for the purpose of limitation.

What is claimed:

1. A ground penetrating radar system comprising:
   a system controller configured to produce an electromagnetic signal for signal penetration of a pavement material;
   a controller configured to produce a frequency modulated electromagnetic wave or a time domain modulated pulsed wave; and
   an ultra wide band (UWB) antenna coupled to the system controller, wherein the UWB antenna is configured to transmit the produced electromagnetic signal to the pavement material and receive the electromagnetic signal as a reflection from the pavement material; and
   wherein the system controller is further configured to:
      receive the electromagnetic signal from the UWB antenna,
      wherein the system controller is further configured for multi use,
      wherein the system controller is capable of switching into a moisture mode or a material mode;
      wherein the system controller is further configured to attain a measurement correlation of at least one of a relative, absolute, or complex permittivity of the pavement material depending on the measurement mode and based on one of a received first reflection signal and a second reflection signal;
      wherein the system controller, when operated in the moisture mode, is further configured to select a moisture calibration curve for a selected pavement material;
      wherein the system controller, when operated in the moisture mode, is further configured to determine the moisture content of the pavement material based on the correlation to dielectric constant or complex permittivity;
      wherein the system controller, when operated in the material mode, is further configured to select a density or thickness calibration curve for a selected asphalt or concrete pavement material;
      wherein the system controller, when operated in the material mode, is further configured to determine a bulk material property of at least one of a density or thickness of the pavement material based on the measurement correlation to the dielectric constant or the complex permittivity; and
      wherein the system controller is configured to select, when in the material mode, one or more system measurement parameters for in situ measurements based on a selected mode corresponding to the pavement material, wherein the pavement material is one of soil, aggregate, sub base, asphalt, concrete, or roller compacted concrete.

2. The ground penetrating radar system of claim 1, wherein a permittivity probe is mounted on to the antenna and in contact with the surface for ground truth data and reducing thickness errors.

3. The ground penetrating radar system of claim 1, wherein the system controller is further configured to determine thickness of the pavement material based on the received electromagnetic signal reflected from the pavement material.

4. The ground penetrating radar system of claim 1, wherein the system controller is further configured to attain a correlation of at least one of a relative, absolute dielectric constant, or complex permittivity of the pavement material based on at least one of a received first frequency reflection signal and second frequency reflection signal.

5. The ground penetrating radar system of claim 4, wherein the system controller is further configured to determine the density of the pavement material based on the measured response correlated to dielectric constant of the pavement material.

6. The ground penetrating radar system of claim 5, wherein the system controller is further configured to determine one of thickness, density, modulus and moisture content of the pavement material based on a frequency difference between the transmitted electromagnetic signal and the received electromagnetic signal.

7. The ground penetrating radar system of claim 6, wherein the system controller is further configured to adjust the determined density of the pavement material based on the correlation of surface roughness of the pavement material.

8. The ground penetrating radar system of claim 7, wherein the system controller is further configured to determine moisture content of the pavement material based on a correlation of the dielectric constant or complex permittivity.

9. The ground penetrating radar system of claim 6, wherein the system controller is further configured to adjust the determined moisture content of the pavement material based on a correlation of determined surface roughness of the pavement material.

10. The ground penetrating radar system of claim 8, wherein the system controller is further configured for dual use, wherein the system controller is capable of switching from a moisture mode to an asphalt mode for changing system parameters relating to asphalt.

11. The ground penetrating radar system of claim 1, wherein the electromagnetic signal is a frequency modulated electromagnetic wave signal.

12. The ground penetrating radar system of claim 1, wherein the electromagnetic signal is a time domain modulated pulse signal.

13. The ground penetrating radar system of claim 1, wherein the pavement material is one of soil, aggregate, rock, asphalt, cement and concrete.

14. The ground penetrating radar system of claim 1, further configured to be coupled with an intelligent compaction unit or intelligent compaction roller.

15. The ground penetrating radar system of claim 14, wherein the system controller is configured to measure thickness of the pavement material.

16. The ground penetrating radar system of claim 14, wherein the system is configured to measure moisture of the pavement material.

17. The ground penetrating radar system of claim 14, wherein the system is configured to measure at least one of density and modulus of the pavement material.

18. The ground penetrating radar system of claim 14, wherein the system is configured to aid in obtaining optimum compaction of a soil by monitoring soil moisture.

19. The ground penetrating radar system of claim 14, wherein the system is configured to aid in obtaining optimum compaction of a soil by monitoring at least one of soil moisture, density, modulus, applied compaction energy, the rolling pattern, and displaying progress on a display.

20. The ground penetrating radar system of claim 1, further comprising a positioning system.

21. A method comprising:
providing a system controller, which is configured for multi use, wherein the system controller is capable of switching into a moisture mode or a material mode; and to set, when in the selected mode, one or more system measurement parameters for in situ measurements based on a selected mode corresponding to the pavement material, wherein the pavement material is one of soil, asphalt, aggregate, sub base, cement, or roller compacted concrete;

producing, by the system controller, an electromagnetic signal for signal penetration of the pavement material, wherein the system controller is a controller configured to produce a frequency modulated electromagnetic wave or time domain modulated pulsed wave;

transmitting, by an ultra wide band (UWB) antenna coupled to the system controller, the produced electromagnetic signal to the pavement material and receive the electromagnetic signal as a reflection from the pavement material; and receiving, by the system controller, the electromagnetic signal from the UWB antenna, attaining, by the system controller, a measurement correlation of at least one of a relative, absolute, or complex permittivity of the pavement material depending on the measurement mode and based on a received at least one of a first reflection signal and a second reflection signal;

selecting, by the system controller when operated in the moisture mode, a moisture calibration curve for a selected pavement material;

determining, by the system controller when operated in the moisture mode, the moisture content of the pavement material based on the correlation to dielectric constant or complex permittivity;

setting, by the system controller when operated in the material mode, a density or thickness calibration curve for a selected asphalt or concrete pavement material;

determining, by the system controller when operated in the material mode, a bulk material property of at least one of a density or thickness of the pavement material based on the measurement correlating to the dielectric constant or the complex permittivity; and setting, by the system controller when in the material mode, one or more system measurement parameters for in situ measurements based on a selected mode corresponding to the pavement material, wherein the pavement material is one of soil, aggregate, asphalt, cement, or roller compacted concrete.

22. The method of claim 21, further comprising obtaining, by the system controller, a quality indicator of the selected pavement material based on the moisture, modulus, density or thickness determined by the in situ measurements correlated from the complex permittivity or dielectric constant measurement response made under the set one or more system measurements parameters of the mode.

23. The method of claim 21, further comprising determining, by the system controller, a positioning measurement and the material measurement, and wherein the method further comprises wirelessly relaying the positioning measurement and the material measurement to a site server, individual computer devices, and the cloud.

* * * * *